US012344876B2

(12) United States Patent
Nguyen et al.

(10) Patent No.: US 12,344,876 B2
(45) Date of Patent: Jul. 1, 2025

(54) SPATIALLY ADDRESSABLE CONTROL OF POLYMERASE ACTIVITY

(71) Applicant: MICROSOFT TECHNOLOGY LICENSING, LLC, Redmond, WA (US)

(72) Inventors: Bichlien Hoang Nguyen, Seattle, WA (US); Jake Smith, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 47 days.

(21) Appl. No.: 17/086,055

(22) Filed: Oct. 30, 2020

(65) Prior Publication Data

US 2022/0136021 A1 May 5, 2022

(51) Int. Cl.
*C12P 19/34* (2006.01)
*C12N 9/12* (2006.01)

(52) U.S. Cl.
CPC ............ *C12P 19/34* (2013.01); *C12N 9/1252* (2013.01); *C12Y 207/07007* (2013.01)

(58) Field of Classification Search
None
See application file for complete search history.

(56) References Cited

U.S. PATENT DOCUMENTS

| | | | | |
|---|---|---|---|---|
| 5,298,414 | A | 3/1994 | Bruce | |
| 7,494,797 | B2 | 2/2009 | Mueller et al. | |
| 10,059,929 | B2 | 8/2018 | Efcavitch et al. | |
| 10,289,801 | B2 | 5/2019 | Church | |
| 10,435,676 | B2 | 10/2019 | Champion et al. | |
| 10,683,536 | B2 | 6/2020 | Efcavitch | |
| 11,414,776 | B2 | 8/2022 | Lin | |
| 2006/0275927 | A1 | 12/2006 | Dubin et al. | |
| 2007/0254327 | A1 * | 11/2007 | Ignatov | C12Q 1/6848 435/25 |
| 2015/0203887 | A1 | 7/2015 | Lazinski et al. | |
| 2018/0274001 | A1 | 9/2018 | Efcavitch et al. | |
| 2019/0323050 | A1 | 10/2019 | Griswold et al. | |
| 2019/0360013 | A1 | 11/2019 | Griswold et al. | |
| 2020/0263152 | A1 | 8/2020 | Magyar et al. | |
| 2020/0362394 | A1 | 11/2020 | Gawad et al. | |
| 2021/0047669 | A1 | 2/2021 | Nguyen | |
| 2021/0071170 | A1 | 3/2021 | Nguyen et al. | |
| 2023/0348946 | A1 | 11/2023 | Nguyen | |

FOREIGN PATENT DOCUMENTS

| | | | | |
|---|---|---|---|---|
| WO | WO-2015113828 | A1 * | 8/2015 | C12N 9/1241 |
| WO | 2017142913 | A1 | 8/2017 | |
| WO | 2017156218 | A1 | 9/2017 | |
| WO | 2017176541 | A1 | 10/2017 | |
| WO | 2017196783 | A1 | 11/2017 | |
| WO | 2017223517 | A1 | 12/2017 | |
| WO | 2018119253 | A1 | 6/2018 | |
| WO | WO-2023154712 | A1 * | 8/2023 | |

OTHER PUBLICATIONS

Ashley, Characterization of a Terminal Deoxynucleotidyl Transferase Activity in Mouse Mammary Tumor Virus, Virology, 77, 367-275, 1977. (Year: 1977).*

Namasivayam, Light-Induced Molecular Cutting: Localized Reaction on a Single DNA Molecule, Anal. Chem., 75, 4188-4194, 2003. (Year: 2003).*

"Non Final Office Action Issued in U.S. Appl. No. 16/543,433", Mailed Date: May 27, 2022, 9 Pages.

"Final Office Action Issued in U.S. Appl. No. 16/563,797", Mailed Date: Jun. 27, 2022, 22 Pages.

"Non Final Office Action Issued in U.S. Appl. No. 16/563,797", Mailed Date: Jan. 18, 2022, 22 Pages.

Hoang, et al., "Modification of 3' Terminal Ends of DNA and RNA Using DNA Polymerase ⊖ Terminal Transferase Activity", In Journal of Bio-Protocol, vol. 7, Issue 12, Jun. 20, 2017, pp. 1-9.

"International Search Report and Written Opinion Issued in PCT Application No. PCT/US21/044861", Mailed Date: Jan. 24, 2022, 17 Pages.

Vortler, et al., "tRNA-Nucleotidyltransferases: Highly Unusual RNA Polymerases with Vital Functions", In Journal of FEBS Letters, vol. 584, Issue 2, Jan. 21, 2010, pp. 297-302.

Thomas, et al., "One-Step Enzymatic Modification of RNA 3' Termini using Polymerase ⊖", In Journal of Nucleic Acids Research, vol. 47, Issue 7, Mar. 1, 2019, pp. 3272-3283.

Barthel, et al., "Enhancing Terminal Deoxynucleotidyl Transferase Activity on Substrates with 3' Terminal Structures for Enzymatic De Novo DNA Synthesis", In Journal of Genes, vol. 11, Issue 1, Jan. 16, 2020, pp. 1-9.

Bellare, et al., "Electrochemical Signal-triggered Release of Biomolecules Functionalized with His-tag Units", In Journal of the Electroanalysis, vol. 31, Issue 11, Jul. 18, 2019, pp. 2274-2282.

Bi, et al., "Building Addressable Libraries: The use of "Safety-Catch" Linkers on Microelectrode Arrays", In Journal of the American Chemical Society vol. 132, Issue 49, Nov. 19, 2010, pp. 17405-17407.

Bollum, FJ., "Terminal Deoxynucleotidyl Transferase", In Journal of the Enzymes, vol. 10, Jan. 1, 1974, pp. 145-171.

Calvert, Paul, "Inkjet Printing for Materials and Devices", In Journal of the Chemistry of Materials, vol. 13, Issue 10, Oct. 15, 2001, pp. 3299-3305.

Cao, et al., "Photo-induced crosslinking of water-soluble polymers with a new photobase generator", In Journal of Polymer, vol. 51, Issue 18, Aug. 19, 2010, pp. 4058-4062.

(Continued)

*Primary Examiner* — Gary Benzion
*Assistant Examiner* — Carolyn L Greene
(74) *Attorney, Agent, or Firm* — Benjamin Keim; Newport IP, LLC

(57) ABSTRACT

Multiple polynucleotides having different, arbitrary sequences are synthesized on the surface of an array by spatial control of polymerase activity. The polymerase is a template-independent polymerase such as terminal deoxynucleotidyl transferase (TdT). Spatial control of polymerase activity is implemented by localized changes in redox-pH conditions. A single species of nucleotide is added and incorporated on growing polynucleotide strands at locations on the array where the polymerase is active. A washing step removes the polymerase and free nucleotides. This process may be repeated multiple times changing both the location of polymerase activity and the species of nucleotide thereby synthesizing different polynucleotides in parallel on the surface of the array. Polymerase activity may be regulated by removing a blocking group attached to a His-tag sequence on the polymerase, a change in pH, or release of encapsulated inhibitors.

20 Claims, 6 Drawing Sheets

(56) References Cited

OTHER PUBLICATIONS

Chu, et al., "Assessing histidine tags for recruiting deoxyribozymes to catalyze peptide and protein modification reactions", In Journal of the Organic & biomolecular chemistry, vol. 14, Issue 20, Apr. 27, 2016, pp. 4697-4703.
Costi, et al., "New Nucleotide—Competitive Non-Nucleoside Inhibitors of Terminal Deoxynucleotidyl Transferase: Discovery, Characterization, and Crystal Structure in Complex with the Target", In Journal of Medicinal Chemistry, Aug. 22, 2013, pp. 7431-7441.
Dimopoulou, et al., "Storing Digital Data Into DNA: A Comparative Study of Quaternary Code Construction", In Proceedings of IEEE International Conference on Acoustics, Speech and Signal Processing, May 4, 2020, pp. 4332-4336.
Egeland, et al., "Electrochemically Directed Synthesis of Oligonucleotides for DNA Microarray Fabrication", In Journal of Nucleic acids research, vol. 33, Issue 14, Aug. 5, 2005, pp. 1-7.
Gangarde, et al., "Amphiphilic Small Molecule Assemblies to Enhance the Solubility and Stability of Hydrophobic Drugs", In Journal of ChemRxiv, Feb. 10, 2020, pp. 1-7.
Hart, et al., "Synthesis and Characterization of trans-Dichlorotetrakis (imidazole)cobalt(III) Chloride: A New Cobalt(III) Coordination Complex with Potential Prodrug Properties", In Journal Bioinorganic Chemistry and Applications, vol. 2018, Article ID 4560757, Sep. 30, 2018, 7 Pages.
Heffern, et al., "Cobalt Derivatives as Promising Therapeutic Agents", In Journal of Current Opinion in Chemical Biology, vol. 17, Issue 2, Apr. 2013, pp. 189-196.
Kobayashi, et al., "Enzymatic synthesis of ligand-bearing DNAs for metal-mediated base pairing utilising a template Independent DNA polymerase", In Journal of Chemical Communications, vol. 52, Issue 19, 2016, 18 Pages.
Lee, et al., "Photon-directed Multiplexed Enzymatic DNA Synthesis for Molecular Digital Data Storage", In Journal of BioRxiv, Feb. 20, 2020., pp. 1-24.
Lee, et al., "Terminator-free Template-independent Enzymatic DNA Synthesis for Digital Information Storage", Published in Nature Communications, vol. 10, Article No. 2383, Jun. 3, 2019, pp. 1-12.
Liang, W., "Encapsulation of ATP into liposomes by different methods: optimization of the procedure", In Journal of the Microencapsulation, vol. 21, Issue 3, May 1, 2004, pp. 251-261.
Liu, et al., "pH-Responsive carriers for oral drug delivery: challenges and opportunities of current platforms", In Journal of the Drug Delivery, vol. 24, Issue 1, Feb. 14, 2017, pp. 569-581.
Motea, et al., "Terminal Deoxynucleotidyl Transferase: The Story of a Misguided DNA Polymerase", Published in Biochimica et Biophysica Acta (BBA)—Proteins and Proteomics, vol. 1804, Issue 5, May 2010, pp. 1151-1166.
Nguyen, et al., "Long-Term Stability and Integrity of Plasmid-Based DNA Data Storage", In Journal of Polymers, vol. 10, Issue 1, Jan. 1, 2018, 10 Pages.
Nguyen, et al., "Microelectrode Arrays: A General Strategy for Using Oxidation Reactions to Site Selectively Modify Electrode Surfaces", In Journal of Langmuir, vol. 30, Issue 8, Mar. 4, 2018, 6 Pages.
Organick, et al., "Random Access in Large-Scale DNA Data Storage", In Journal of the Nature Biotechnology, vol. 36, Issue No. 3, Mar. 2018, pp. 242-248.
Palluk, et al., "De novo DNA synthesis using polymerase-nucleotide conjugates", In Journal of Nature Biotechnology, vol. 36, Issue 7, Jul. 2018, 11 Pages.
Pandey, et al., "Inhibition of terminal deoxynucleotidyl transferase by adenine dinucleotides", In Journal of FEBS Letters, vol. 213, Issue 1, Mar. 9, 1987, pp. 204-208.
"International Search Report and Written Opinion Issued in PCT Application No. PCT/US20/037104", Mailed Date: Sep. 28, 2020, 10 Pages.
"International Search Report and Written Opinion Issued in PCT Application No. PCT/US20/038020", Mailed Date: Sep. 21, 2020, 12 Pages.
Richey, et al., "Mg Anode Corrosion in Aqueous Electrolytes and Implications for Mg-Air Batteries", In Journal of the Electrochemical Society, vol. 163, Issue 6, Mar. 14, 2016, pp. A958-A963.
Romero, et al., "Organic Photoredox Catalysis", In Journal of Chemical Reviews, vol. 116, No. 17, Sep. 14, 2016, pp. 10075-10166.
Shaw, et al., "Photoredox Catalysis in Organic Chemistry", In Journal of the Organic Chemistry , vol. 81, Issue 16, Aug. 1, 2016, pp. 6898-6926.
Shi, et al., "Long-Lived Photoacid Based upon a Photochromic Reaction", In Journal of the American Chemical Society, vol. 133, No. 37, Sep. 21, 2011, pp. 14699-14703.
Waters, et al., "Effect of Chelation on Iron-Chromium Redox Flow Batteries", In Journal of the ACS Energy Letters, vol. 5, No. 6, Apr. 30, 2020, pp. 1758-1762.
Yoshida, et al., "Effects of Metal Chelating Agents on the Oxidation of Lipids Induced by Copper and Iron", In Journal of Biochimica et Biophysica Acta (BBA)—Lipids and Lipid Metabolism vol. 1210, Issue 1, Dec. 2, 1993, pp. 81-88.
"Notice of Allowance Issued in U.S. Appl. No. 16/543,433", Mailed Date: Feb. 8, 2023, 8 Pages.
"Notice of Allowance Issued in U.S. Appl. No. 16/543,433", Mailed Date: Apr. 14, 2023, 6 Pages.
"Notice of Allowance Issued in U.S. Appl. No. 16/563,797", Mailed Date: Jun. 16, 2023, 8 Pages.
Riguero, et al., "Immobilized Metal Affinity Chromatography Optimization for Poly-histidine Tagged Proteins", In Journal of Chromatography A, vol. 1629, Aug. 21, 2020, pp. 1-19.
Ghindilis, et al., "Enzyme-Catalyzed Direct Electron Transfer: Fundamentals and Analytical Applications", In journal of Electroanalysis, vol. 9, Issue 9, Feb. 10, 1997, pp. 661-674.
Kuznetsova, et al., "Insight into the Mechanism of DNA Synthesis by Human Terminal Deoxynucleotidyltransferase", In Journal of Life Science Alliance, vol. 5, Issue 12, Aug. 1, 2022, pp. 1-16.
Ganesana, et al., "Site-specific Immobilization of a (His)6-Tagged Acetylcholinesterase on Nickel Nanoparticles for Highly Sensitive Toxicity Biosensors", In Journal of Biosensors and Bioelectronics, vol. 30, Issue 1, Dec. 15, 2011, pp. 43-48.
Final Office Action mailed on Dec. 30, 2024, in U.S. Appl. No. 18/221,364, 10 pages.
Non-Final Office Action mailed on Aug. 23, 2024, in U.S. Appl. No. 18/221,364, 11 pages.
Notice of Allowance mailed on Mar. 29, 2023, in U.S. Appl. No. 16/543,433, 6 Pages.
Notice of Allowance mailed on Apr. 22, 2025, in U.S. Appl. No. 18/221,364, 09 Pages.

* cited by examiner

SPATIALLY ADDRESSABLE CONTROL OF POLYMERASE ACTIVITY

BACKGROUND

Synthetic oligonucleotides, also referred to as polynucleotides, such as deoxyribonucleic acid (DNA) and ribonucleic acid (RNA) have uses in medicine, molecular biology, nanotechnology, data storage, and other applications. Enzymatic polynucleotide synthesis has emerged as an alternative to the long-standing nucleoside phosphoramidite method for synthesis of polynucleotides. Enzymatic polynucleotide synthesis is performed with a template-independent polymerase such as terminal deoxynucleotide transferase (TdT) rather than a series of chemical reactions. Enzymatic polynucleotide synthesis has advantages over the nucleoside phosphoramidite method because it is performed in an aqueous environment and does not use toxic organic chemicals. Enzymatic polynucleotide synthesis also has the potential to create longer polynucleotides than the nucleoside phosphoramidite method.

However, template-independent polymerases add nucleotides in an unregulated manner. These polymerases can add any available nucleotide and can create random sequences if provided with multiple types of nucleotides. If only a single species of nucleotide is present, the nucleotide may be added repeatedly creating variable length homopolymers. Thus, it is challenging to precisely control the base-by-base sequence of polynucleotides created through enzymatic polynucleotide synthesis. In contrast, with the established nucleoside phosphoramidite method, each synthesis cycle reliably adds only a single, specific nucleotide.

Techniques for highly parallel and automated enzymatic-based methods are clearly desirable for many applications such as digital data storage. However, controlling the enzymes used for polynucleotide synthesis brings unique challenges that are not present in chemical phosphoramidite synthesis. This disclosure is made with respect to these and other considerations.

SUMMARY

This disclosure provides methods and devices for de novo array-based enzymatic solid-phase synthesis of polynucleotides. Spatially addressable control of polymerase activity on the surface of an array allows for parallel synthesis of multiple polynucleotides with different sequences. The spatial control is provided by regulating the activity of a template-independent polymerase such as TdT.

Spatial addressability, the ability to turn polymerization "on" or "off" at selected locations on an array, enables the synthesis of polynucleotides of different sequences on the same array. Polymerases are activated on a selected location on the surface of the array, a single species of nucleotide is provided, and that nucleotide is incorporated into growing polynucleotide strands at the selected location. Nucleotide addition does not occur to an appreciable degree at locations where the polymerase is not activated. A reaction reagent solution covering the array is washed away and polynucleotide extension stops. This process is repeated multiple times. The selected location and the selected nucleotide species may both be independently changed in subsequent rounds of addition. With this technique, polynucleotides with different, arbitrary sequences are synthesized on the surface of the array.

In a first implementation, activity of the template-independent polymerase is regulated by the presence or absence of a blocking group attached to the enzyme. The blocking group may be a protein or polymer that is attached to the template-independent polymerase by a His-tag. The blocking group sterically hinders access to the active site on the polymerase preventing activity. His-tags are complexed to a ligand on the blocking group with divalent metal cations such as $Cu^{2+}$. Changing the oxidation state of the metal cation from 2+ breaks the His-tag complex and releases the blocking group from the template-independent polymerase. Thus, the polymerase becomes active only in those locations where the oxidation state of the metal cation is changed. The oxidation state of the metal cation may be changed by redox reactions initiated through electrodes, addition of chemical redox reagents, or excitation of photoredox catalysts. Activation of the polymerase is confined to the selected location by an excess of divalent metal cations in the reaction reagent solution. The divalent metal cations cause the blocking group to reattach to the His-tag if a polymerase moves away from the selected location.

In a second implementation, activity of the template-independent polymerase is regulated by pH. The polymerase and selected nucleotide species may be provided in a solution with a pH that inactivates the polymerase—an "unsuitable pH." The pH of the solution at a selected location on the surface of the array is changed from the unsuitable pH to an optimum pH for the polymerase. The polymerase becomes active at the selected location but not at other locations due to the localized pH change. The pH of the solution may be changed by activation of electrodes, addition of an acid or base, or photoactivation of a photoacid or a photobase. The change in pH is confined to the selected location by a buffer in a reaction reagent solution.

In a third implementation, activity of the template-independent polymerase is regulated by the presence of enzyme inhibitors such as adenosine triphosphate (ATP). The enzyme inhibitors are encapsulated or otherwise inactivated in solution. Thus, the polymerase is active at all locations where the enzyme inhibitors are encapsulated. Release of the enzyme inhibitors from encapsulation by a change in pH inactivates the polymerase. The enzyme inhibitors may be released from encapsulation at a selected location by a localized change in pH. The pH may be changed by any of the techniques mentioned above. In this implementation, unlike the first and second implementations, the polymerase is inactivated rather than activated at the selected location. This technique may lead to some level of nucleotide incorporation across the entire array but there will be much less at the locations where inhibitors are released. The different lengths of polynucleotide extension may be used to encode information even if they do not have precisely specified base-by-base sequences.

To prevent incorporation of nucleotides across the entire surface of the array before release of enzyme inhibitors, a different mechanism may initially keep the polymerase inactive. For example, the temperature of a solution containing the template-independent polymerase may be kept at a low temperature at which the polymerase is has substantially reduced activity. After the enzyme inhibitors are released from encapsulation, the temperature is increased and the polymerase becomes active. Nucleotides are added to the growing polynucleotide strands at locations other than the selected location. At the selected location, nucleotides are not added or added at a greatly reduced rate due to the presence of inhibitors.

Array-based synthesis of polynucleotides improves the scalability and throughput of previous enzymatic synthesis techniques that use beads in a test tube for solid-phase synthesis. All polynucleotides synthesized in the same test tube, plate well, or reaction chamber are exposed to the same conditions and thus will have the same sequence of nucleotides. This requires a physically separate reaction environment for each unique polynucleotide sequence that is synthesized. However, array-based synthesis techniques in which localized reaction environments (e.g., redox conditions or pH) can be changed on the surface of the array provide the ability to synthesize polynucleotides with different sequences on the same array. This design is more compact and requires less physical manipulation than a comparable system in which each unique polynucleotide sequence must be created in a different tube or well.

This disclosure also provides a device for de novo synthesis of polynucleotides using an array and a reaction reagent solution containing template-independent polymerase. This device may include fluid delivery pathways for adding the reaction reagent solution and selected species of nucleotides to the surface of the array. The device may control redox-pH conditions on the surface of the array through any number of different techniques. In an implementation, the array is a microelectrode array with individually addressable electrodes that can change a local redox-pH environment upon activation. In an implementation, a targeted fluid deposition instrument such as a chemical inkjet printer may be used to add small volumes of redox reagent, acid, or base to specific locations on the surface of the array. In an implementation, a light source capable of inducing a photoredox reaction by exciting a photoredox catalyst or changing pH by activation of a photoacid or photobase may be directed onto specific locations on the surface of the array.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
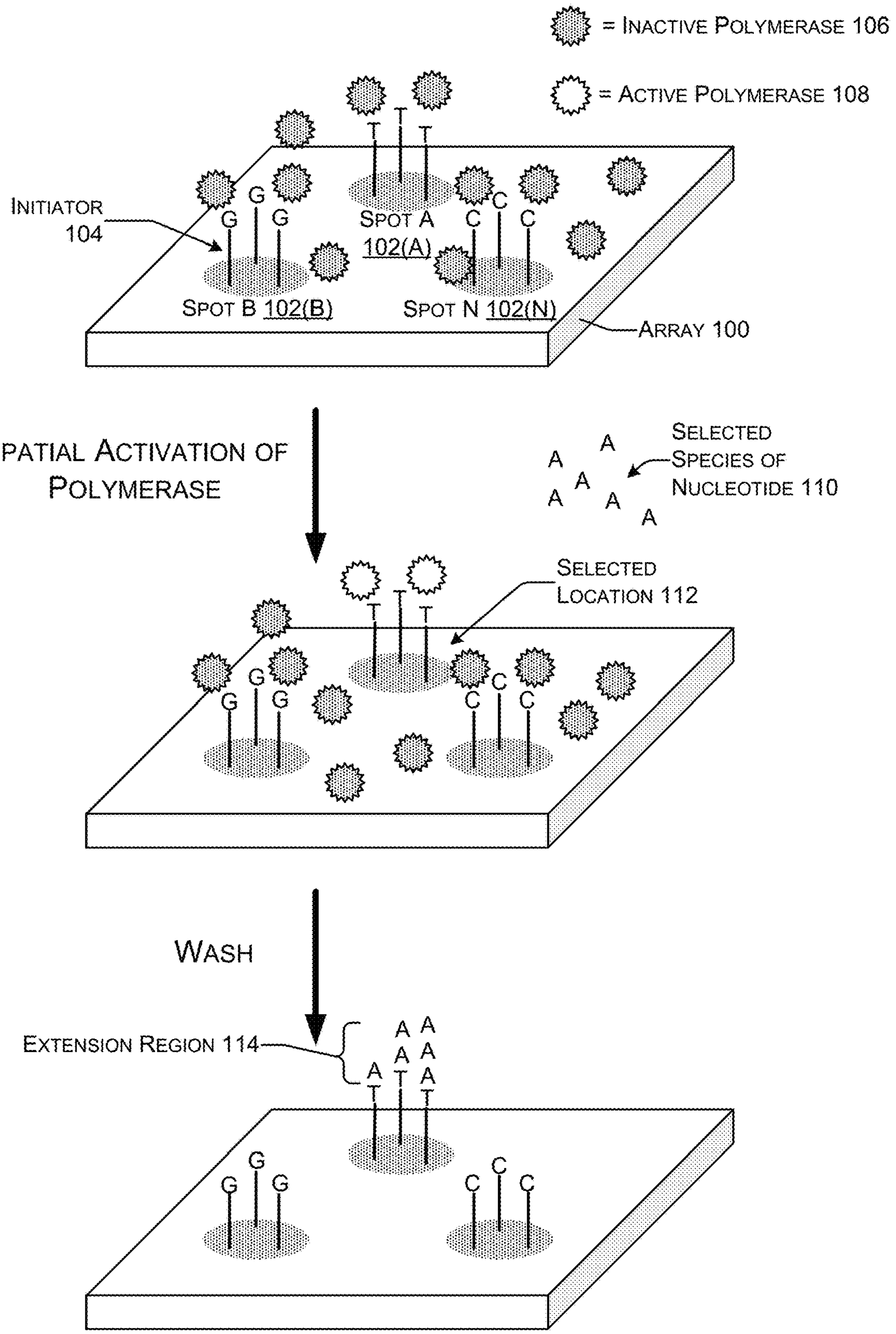
FIG. 1 shows solid-phase polynucleotide synthesis on an array using spatial control of polymerase activity.

This disclosure provides techniques for solid-phase de novo synthesis of polynucleotides with arbitrary sequences by location-specific control of template-independent polymerase activity. Many existing techniques for enzymatic synthesis of polynucleotides control polymerization by regulating availability of nucleotides rather than polymerase activity. The techniques of this disclosure are thus able to use unmodified nucleotides rather than requiring nucleotides attached to a blocking group. This disclosure describes multiple techniques for controlling polymerase activity in a location-specific manner. These techniques include use of a His-tag to attach a blocking group to a polymerase, regulation of pH to prevent polymerase activity, and selective release of encapsulated enzyme inhibitors. Moreover, the techniques of this disclosure regulate enzyme activity without changing the availability of a metal cofactor necessary for functioning of the template-independent polymerase. Availability of a metal cofactor refers to the presence of a suitable metal cofactor in the appropriate oxidation state at sufficient concentration for polymerases activity. A metal cofactor may be made unavailable by multiple techniques including, but not limited to, sequestration such as with a ligand or by changing its oxidation state.

There are many uses for synthetic polynucleotides having specified sequences such as basic research, medicine, and nanoengineering (e.g., DNA origami). One relatively recent application for synthetic polynucleotides is digital data storage. Polynucleotides such as DNA may be used to store digital information by designing a sequence of nucleotide bases that encodes the zeros and ones of the digital information. There are various techniques and encoding schemes known to those of skill in the art for using nucleotide bases to represent digital information. See Lee Organick et al., *Random Access in Large-Scale DNA Data Storage,* 36:3 Nat. Biotech. 243 (2018) and Melpomeni Dimpoulou et al., *Storing Digital Data Into DNA: A Comparative Study of Quaternary Code Construction*, ICASSP Barcelona, Spain (2020). Advantages of using polynucleotides rather than another storage media for storing digital information include information density and longevity. The sequence of nucleotide bases is designed on a computer and then polynucleotides with those sequences are synthesized. The polynucleotides may be stored and later read by a polynucleotide sequencer to retrieve the digital information.

Polynucleotides, also referred to as oligonucleotides, include both DNA, RNA, and hybrids containing mixtures of DNA and RNA. DNA includes nucleotides with one of the four natural bases cytosine (C), guanine (G), adenine (A), or thymine (T) as well as unnatural bases, noncanonical bases, and/or modified bases. RNA includes nucleotides with one of the four natural bases cytosine, guanine, adenine, or uracil (U) as well as unnatural bases, noncanonical bases, and/or modified bases. Nucleotides include both deoxyribonucleotides and ribonucleotides covalently linked to one or more phosphate groups.

Template-independent polymerases are DNA or RNA polymerases that perform de novo oligonucleotide synthesis without use of a template strand. Currently known template-independent polymerases include TdT and tRNA nucleotidyltransferase. TdT as used herein includes both the full-length wild-type enzyme, as well as modified enzymes that are truncated or internally modified. One example of modified TdT is provided in U.S. Pat. No. 10,059,929. An example of truncated TdT is provided in U.S. Pat. No. 7,494,797. Thus, template-independent polymerase as used herein includes full-length wild-type, truncated, or otherwise modified TdT, tRNA nucleotidyltransferase, and any subsequently discovered or engineered polymerases that can perform template-independent synthesis of polynucleotides.

Template-independent polymerase as used herein does not encompass modifications that render an enzyme incapable of performing nucleotide polymerization.

TdT is a protein that evolved to rapidly catalyze the linkage of naturally occurring deoxynucleotide triphosphates (dNTPs). Native TdT is a very efficient enzyme. It has been demonstrated that TdT can polymerize extremely long homopolydeoxynucleotides of 1000 to 10,000 nucleotides in length (see Hoard et al., *J. of Biol. Chem.,* 1969 244(19): 536373; F. J. Bollum, *The Enzymes*, Volume 10, New York: Academic Press; 1974. p. 141-71; Tjong et al., *Anal. Chem.* 2011, 83:5153-59. TdT adds nucleotides indiscriminately to the 3' hydroxyl group at the 3' end of single-stranded DNA. TdT performs unregulated synthesis adding any available dNTP. TdT uses an existing polynucleotide referred to as an "initiator" as the starting point for synthesis. Initiators as short as three nucleotides have been successfully used with TdT for enzymatic synthesis of DNA. Suitable initiator length ranges from three nucleotides to about 30 nucleotides or longer. Initiators may be single stranded or double stranded. Double stranded initiators may have a 3' overhang or they may be blunt ended or they may have a 3' recessed end. During polymerization, the template-independent polymerase holds a DNA strand (which initially is only the initiator but grows as synthesis proceeds) and adds dNTPs in a 5'-3' direction. TdT activity is maximized at approximately 37° C. and performs enzymatic reactions in an aqueous environment.

Because TdT performs unregulated synthesis, using this enzyme to create a polynucleotide with a pre-specified arbitrary sequence requires regulation and control of the TdT activity. One technique to regulate TdT activity is limiting the available nucleotides to only a single type of deoxynucleoside triphosphate (dNTP) or nucleoside triphosphate (NTP) (e.g., only deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP)). Thus, providing only one choice forces the polymerase to add that type of nucleotide.

However, this does not prevent TdT from adding the nucleotide multiple times thereby creating homopolymers. Techniques for limiting homopolymer creation by TdT include using nucleotides with removable protecting groups that prevent addition of more than one nucleotide at a time. Examples of techniques that use blocking groups attached to nucleotides are described in U.S. Pat. Nos. 10,059,929 and 10,683,536. These techniques require specially modified dNTPs.

Another technique for enzymatic synthesis uses TdT enzymes each tethered to a single dNTP by a cleavable linker. See Sebastian Palluk et al., De novo *DNA synthesis using polymerase-nucleotide conjugates,* 36(7) Nature Biotechnology 645 (2018) and WO 2017/223517 A1. In this system dNTPs are modified by attachment to TdT.

A third technique for nucleotide synthesis using TdT regulates polymerization by including the enzyme apyrase, which degrades nucleoside triphosphates into their TdT-inactive diphosphate and monophosphate precursors. In this technique, apyrase limits polymerization by competing with TdT for nucleoside triphosphates. See Henry H. Lee et al., *Terminator-free template-independent Enzymatic DNA Synthesis for Digital Information Storage,* 10:2383 Nat. Comm. (2019) and WO 2017/176541 A1. Although unmodified nucleotides may be used in this technique, it is nucleotide availability rather than enzyme activity that is controlled.

Although the above techniques may be used to limit the "extension length" or average number of nucleotides added during a cycle of synthesis, they do not describe synthesis of multiple polynucleotides with different sequences on a single array. These solid-phase enzymatic nucleotide synthesis techniques involve initiators attached to beads in a test tube or other discrete reaction chamber. The reaction chamber is flooded with an aqueous solution containing TdT and only one type of dNTP. Once coupling has taken place, the TdT and any free dNTPs are washed away. The beads are incubated in a second step with TdT and a different dNTP. The process continues creating DNA molecules with sequence specified by the order in which the different dNTPs are added. Depending on the control technique used, TdT may add a single nucleotide or an uncontrolled number of the same nucleotide during each cycle synthesis. This process does not scale well for applications that require high throughput synthesis of multiple polynucleotides with different sequences.

There are techniques that provide spatial control of template-independent polymerase on an array. These techniques do so by regulating the availability of metal cofactors that are necessary for enzyme activity. One technique keeps the metal cofactors in an inactive state by caging with DMNP-EDTA and releases the metal cofactors at specific locations by exposure to patterned UV light. Diffusion of the metal cofactors is controlled by providing an excess of the caging molecules. The TdT and nucleotides are provided in a standard synthesis master mix. See Howon Lee et al., *Photon-directed Multiplexed Enzymatic DNA Synthesis for Molecular Digital Data Storage*, bioRxiv 2020.02.19.956888.

A different technique also by the inventors of this application, controls the oxidation state of metal enzyme cofactors. The metal cofactors are changed from an oxidation state of +2 that complexes with the enzyme to a different oxidation state that does not. Template-independent polymerase is inactive unless metal cofactors with an oxidation state of +2 are available. Spatial control of the oxidation state is achieved by activation of electrodes on a microelectrode array, controlled addition of redox reagents, or other techniques. Diffusion of the metal cofactors in the +2 oxidation state is controlled by scavenger molecules that either change the oxidation state or sequester the metal cofactors. See U.S. patent application Ser. No. 16/543,433 filed on Aug. 16, 2019, with the title "Regulation of Polymerase Using Cofactor Oxidation States." However, control of metal cofactor availability is only one way of regulating polymerase activity.

Detail of procedures and techniques not explicitly described or other processes disclosed in this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, $4^{th}$ ed. (2012).

FIG. 1 shows an illustrative representation of solid-phase synthesis on an array 100 in which the location of nucleotide addition is regulated by controlling activity of a template-independent polymerase. The array 100 provides a solid support for solid-phase synthesis of polynucleotides. Solid-phase synthesis is a method in which molecules are covalently bound on a solid support material and synthesized step-by-step in a single reaction vessel. The polymerase is a template-independent polymerase such as TdT. The template-independent polymerase may be obtained from a number of sources such as isolation from calf thymus or a recombinant source (e.g., a genetically modified *E. coli* strain). In some implementations, the template-independent polymerase is synthesized chemically or using recombinant techniques in order to add a His-tag.

The array 100 may be made of any material that is capable of anchoring polynucleotides. The array 100 may be formed from a silicon chip, glass (e.g., controlled porous glass (CPG)), an insoluble polymer, or other material. The array 100 being a generally flat two-dimensional surface provides for addressable, site-specific manipulations at specified locations (e.g., represented in terms of x- and y-coordinates) on the surface of the array 100. The array 100 may be an electrochemically inert surface or it may include an array of individually addressable microelectrodes.

Examples of microelectrode arrays are provided in Bo Bi et al., *Building Addressable Libraries: The Use of "Safety-Catch" Linkers on Microelectrode Arrays,* 132 J. Am. Chem. Soc. 17,405 (2010); Bichlien H. Nguyen et al., *Microelectrode Arrays: A General Strategy for Using Oxidation Reactions To Site Selectively Modify Electrode Surfaces,* 30 Langmuir 2280 (2014); and U.S. patent application Ser. No. 16/435,363 filed on Jun. 7, 2019, with the title "Reversing Bias in Polymer Synthesis Electrode Array." One example of a microelectrode array and techniques for attaching polynucleotides to the surface of the array is provided in a Ryan D. Egeland & Edwin M. Southern, *Electrochemically Directed Synthesis of Oligonucleotides for DNA Microarray Fabrication,* 33(14) Nucleic Acids Res. e125 (2005).

The electrodes in a microelectrode array may be implemented with any known technology for creating microelectrodes such as complementary metal-oxide-semiconductor (CMOS) technology. CMOS may include metal-oxide-semiconductor field-effect transistors (MOSFETs) made through a triple-well process or by a silicon-on-insulator (SOI) process. A series of controllable gates/transistors implemented with CMOS circuits can be controlled to inject charge at any location on the surface of the microelectrode array. Each electrode in the microelectrode in the array may be independently addressed allowing the creation of arbitrary and variable voltage microenvironments across the surface of the microelectrode array.

High microelectrode density allows for fine-scale level control of the ionic environment at the surface of the microelectrode array. A microelectrode array may have a microelectrode density of approximately 1024 microelectrodes/$cm^2$, approximately 12,544 microelectrodes/$cm^2$, or a different density.

The array 100 may be covered with a plurality of spots 102(A), 102(B), . . . , 102(N) at which initiators 104 are attached. Each of the initiators 104 is a single- or double-stranded polynucleotide strand. If double-stranded, the initiators 104 may have a 3' overhang, they may be blunt ended, or they may have a 3' recessed end. The length of an initiator 104 may be about 3-30 nucleotides, about 15-25 nucleotides, or about 20 nucleotides. The initiators 104 are not shown to scale. Because they are lengthened through repeated rounds of nucleotide addition, the initiators 104 may be referred to as growing (single-stranded) polynucleotide strands.

Although only three spots 102(A), 102(B), 102(N) are shown in this illustrative representation many thousands or hundreds of thousands of spots may be present on a typical array 100. The size of a single spot 102 can be smaller than about 1 $cm^2$, smaller than about 1 $mm^2$, smaller than about 0.5 $mm^2$, smaller than about 100 $\mu m^2$, smaller than about 50 $\mu m^2$, smaller than about 1 $\mu m^2$, smaller than about 500 $nm^2$, or smaller than about 200 $nm^2$. Initiators 104 may also be present on the array 100 at locations other than the spots 102.

The initiators 104 may be attached to the array 100 using any known technique for anchoring single-stranded DNA or RNA to a solid support such as techniques used in conventional solid-phase synthesis of polynucleotides or used for creation of DNA microarrays. For example, the initiators 104 may be spotted onto the array 100 by use of a robot to "print" pre-designed nucleotide sequences using fine-pointed pins, needles, or ink-jet printing onto a chemical matrix surface using surface engineering. Other methods employ photo-activated chemistry and masking to synthesize the initiators 104 one nucleotide at a time on the solid surface of the array 100 with a series of repeated steps to build up the initiators 104 at designated locations. In some implementations, the surface of the array 100 may be functionalized and the initiators 104 may be attached to the functional groups rather than directly to the array 100.

All of the initiators 104 attached to the array 100 may have the same or approximately the same nucleotide sequence or one or more of the initiators 104 may have different sequences from the others. The sequence of any one or more of the initiators 104 may be a random sequence of nucleotides. The initiators 104 may also be constructed with non-random sequences such as, for example, sequences that are cleaved by a specific restriction endonuclease. Cleavage of the initiators 104 is one way to release completed polynucleotides from the surface of the array 100. The sequences of the initiators 104 may also be designed or used as primer binding sites for subsequent amplification (e.g., polymerase-chain reaction (PCR) amplification) of fully synthesized polynucleotides.

Each spot 102 on the array 100 may contain many tens or hundreds of initiators 104 although for simplicity only three initiators 104 are shown on each spot 102 in this illustrative representation. Each initiator 104 attached to a single spot 102 is subject to the same spatially addressable control. Stated differently, any spatially addressable activation of a polymerase applied to the array 100 is performed at the resolution of individual spots 102. However, the polynucleotides synthesized on the same spot 102 do not necessarily have the same nucleotide sequence because of the formation of variable length homopolymers.

The array 100 may be covered with a reaction reagent solution that contains inactive polymerase 106. The reaction reagent solution is an aqueous solution that includes the polymerase and may also include buffers, salts, electrolytes, and the like. For example, the aqueous solution may include TdT buffer and a $CoCl_2$ solution to supply metal cofactors for the polymerase. There are many techniques for inactivating polymerase which are discussed in greater detail herein including blocking groups, unsuitable pH conditions, and enzyme inhibitors. Inactive polymerase 106 does not polymerize the addition of nucleotides to a growing polynucleotide strand or does so at a rate that is substantially less than the maximum rate of polymerization. For example, inactive polymerase 106 that still retains polymerase activity may perform nucleotide polymerization at rate that is less than 5%, 10%, 20%, 30%, or 40% of the maximum polymerization rate of the enzyme. Techniques for measuring DNA polymerase activity are known to those of ordinary skill in the art and described in WO 2010/036359.

Spatial activation of the polymerase creates active polymerase 108 at one or more of the spots 102 on the array 100. Active polymerase 108 may be created by modifying inactive polymerase 106 or altering conditions such that the polymerase changes to an active state. For example, a blocking group attached to an inactive polymerase 106 may be released creating active polymerase 106. The pH of the reaction reagent solution may be changed from a pH that prevents enzyme activity to an optimum pH for the polymerase that enables enzyme activity. Active polymerase 108 catalyzes the addition of nucleotides to the 3'-end of a growing polynucleotide strand. Initially the growing polynucleotide strand is the initiator 104. An active polymerase 108 may perform nucleotide polymerization at a rate that is at least 90%, 80%, 70%, or 60% of the maximum rate of polymerization for the polymerase.

In an alternative implementation (not shown in this figure) encapsulated enzyme inhibitors may be released from encapsulation thereby inhibiting polymerase activity. In this implementation, the array 100 is initially covered with active polymerase 108 that is changed to inactive polymerase 106 over one or more spots 102 where the enzyme inhibitors are released. The encapsulated enzyme inhibitors may be included in the reaction reagent solution.

In the illustrated representation, the inactive polymerase 106 located at spot A 102(A) is changed to active polymerase 108. This makes it possible for nucleotides to be incorporated onto the ends of the initiators 104 at spot A 102(A) during the next synthesis cycle. Each added nucleotide extends the initiator 104 which becomes a growing polynucleotide strand. In a synthesis cycle, the surface of the array 100 may be flooded with a reaction reagent solution that contains inactive polymerase 106 and a selected species nucleotide 110 (i.e., a nucleotide having a specified base such as A, C, G, T, or U). Addition of only a single species of nucleotide limits the template-independent polymerase from randomly adding any nucleotide species. A nucleotide is a nucleoside linked to one or more phosphate groups. In some implementations, a nucleotide may be a deoxynucleoside triphosphate (dNTP) or a ribose triphosphate (NTP). Nucleotides are not limited to the canonical nucleotides but may also include nucleotide analogs.

In this example, a selected location 112 is defined by areas on the array 100 where the inactive polymerase 106 is changed to an active polymerase 108. This representation shows the selected location 112 as spot A 102(A). The selected location 112 may be any one or more locations that are contiguous or separate on the surface of the array 100. The selected location 112 may be a single spot 102, a group of spots located adjacent to each other, or multiple disparate spots spread across the surface of the array 100. In some implementations, the selected location 112 has an area less than 100 $\mu m^2$, about 650 $nm^2$, or about 200 $nm^2$. The resolution or minimum size of the selected location 112 may be a single spot 102. The spots 102 may be spaced apart from each other creating a buffer zone that functions to prevent nucleotide incorporation that spills over the edge of one spot 102(A) from adding nucleotides to an adjacent spot 102(B).

Alternatively, if polymerase activity is controlled by enzyme inhibitors, release of enzyme inhibitors from encapsulation at the selected location 112 changes an active polymerase 108 to an inactive polymerase 106. Thus, in this implementation the polymerase is inactive at the selected location 112 and active everywhere else.

The selected species of nucleotide 110 in this illustrative representation includes the base adenine (A) such as dATP or ATP. The selected species of nucleotide 110 may be provided as free nucleotides in solution. The free nucleotides are added to the 3'-ends of initiators 104 where there is active polymerase 108. In an implementation, the selected species of nucleotide 110 may be an unmodified nucleotide that does not include a blocking group or any other modification. An unmodified nucleotide is a standard dNTP or NTP.

After the polymerase has had time to react with free nucleotides in solution (e.g., about 10, 20, 30, 40, 50 seconds, 1 minute, or 2 minutes) a wash step may be used to remove the polymerase and free nucleotides stopping extension of the initiators 104. Depending on the length of time active polymerase 108 is in contact with the initiators 104, multiple unmodified nucleotides may be added creating a homopolymer. Thus, the polynucleotide synthesis techniques of this disclosure may create block polymers in which the base-by-base sequence of polynucleotides on the same spot 102 is not always identical. However, the order of nucleotide blocks will be the same.

For example, a first cycle of synthesis may add from one to three adenine nucleotides to the 3' end of the initiators 104 at spot A 102(A). Additional nucleotides added during a single cycle of synthesis are referred to as extension region 114. This variation arises from the ability of template-independent polymerases to perform unregulated polymerization. Under a given set of reaction conditions the number of nucleotides added in an extension region 114 will vary with a distribution concentrated around a mean extension length. The reaction conditions include temperature, time, and the concentrations of the nucleotide, and concentration of the template-independent polymerase. The extension length may be tuned by adjusting the reaction time.

Thus, unless context indicates otherwise, "extension length" refers to the average extension length for a given set of reaction conditions. This variation in extension length for individual ones of the polynucleotides is the reason why a population of polynucleotides at the same spot 102 may have different sequences. Due to the presence of homopolymers it may not be possible to synthesize polynucleotides with specific base-by-base sequences using unmodified nucleotides.

However, polynucleotides that have a specified order of nucleotide bases even if the precise number of nucleotides is not controllable have uses in applications such as digital data storage. Data may be included in nucleotide transitions rather than by the absolute sequence. Techniques for encoding digital data using nucleotide transitions in polynucleotides with homopolymers are discussed in Henry H. Li et al., *Terminator-free template-independent enzymatic DNA synthesis for Digital information storage.* 10:2383 Nat. Comm. (2019), WO 2017/176541 A1, and U.S. patent application Ser. No. 16/543,433 filed on Aug. 16, 2019, with the title "Regulation of Polymerase Using Cofactor Oxidation States."

In some implementations, the selected species of nucleotide 110 may be modified such as by addition of a 3' protecting group. Techniques for creating modified nucleotides that include a 3' protecting group are known to those of skill in the art. Illustrative 3' protecting groups are described in U.S. patent application Ser. No. 16/886,638 filed on May 28, 2020, with the title "De novo polynucleotide synthesis with substrate-bound polymerase."

The selected species of nucleotide 110 is added to the 3'-end of an initiator 104 and the 3' protecting group remains preventing further nucleotide addition. Thus, by use of modified nucleotides with protecting groups the synthesis techniques of this disclosure can be used to create polynucleotides with specific base-by-base sequences. Once the active polymerase 108 is removed either by a wash step or by conversion to inactive polymerase 106 the blocking groups on the ends of the initiators 104 are removed and the cycle can be repeated.

However, if homopolymers can be tolerated in the final polynucleotides, use of unmodified nucleotides provides a cost benefit because unmodified nucleotides are less expensive than modified nucleotides. For example, dNTPs with protecting groups such as CleanAmp® dNTPs available from TriLink® Biotechnologies cost approximately 2.5 times more than equivalent unprotected dNTPs.

Figure 2:
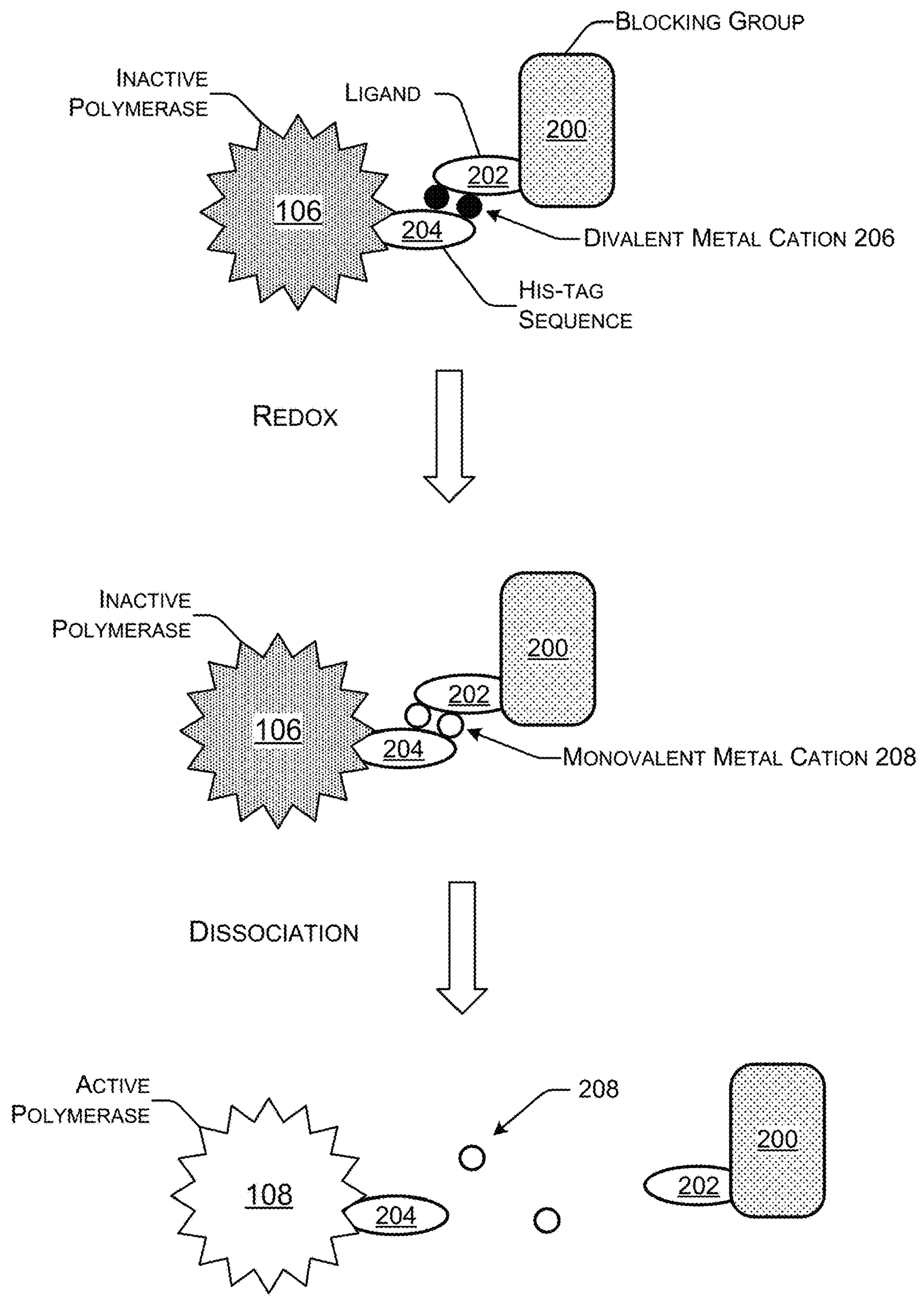
FIG. 2 shows use of a blocking group attached by a His-tag sequence to regulate polymerase activity.

FIG. 2 shows use of a blocking group 200 reversibly attached by a His-tag sequence 204 as one technique to regulate polymerase activity. When the blocking group 200 is attached it sterically hinders activity of the polymerase. The polymerase is then unable to add nucleotides to the end of a growing polynucleotide strand or the rate of addition is greatly slowed. The blocking group 200 may include a ligand 202 that is complexed to a His-tag sequence 204 on the polymerase. In an implementation, the blocking groups 200 are covalently modified with ligands 202. The polymerase is an inactive polymerase 106 when the blocking group 200 is attached and becomes an active polymerase 108 when the blocking group is detached.

A polymerase, such as TdT, may be covalently modified with a polyhistidine tag or His-tag sequence 204. Polymerases that include a His-tag sequence 204 may be created by well-known protein production process including expression in *E. coli* or yeast. The His-tag sequence 204 may be added to the N-terminal or the C-terminal of the polymerase. Modifications of TdT to include a His-tag for protein purification are described in U.S. Pat. Nos. 10,435,676, 10,059,929, U.S. Pat. Pub. No. 2019/0360013, and Sebastian Barthel et al., *Enhancing Terminal Deoxynucleotidyl Transferase Activity on Substrates with 3′ Terminal Structures for Enzymatic De Novo DNA Synthesis,* 11 Genes 102 (2020). Proteins may also be synthesized with His-tags using techniques such as those described in Chih-Chi Chu and Scott K. Silverman, *Assessing histidine tags for recruiting deoxyribozymes to catalyze peptide and protein modification reactions,* 14 Org. Biomol. Chem 4697 (2016).

A His-tag sequence 204 binds metal centers such as certain divalent metal cations 206. The behavior of polyhistidine tags is known to those of ordinary skill in the art and discussed in Richard J. Sundberg and R. Bruce Martin, *Interactions of histidine and other imidazole derivatives with transition metal ions in chemical and biological systems,* 74(4) Chem Rev. 471 (1974). The divalent metal cation 206 may be a transition metal. The divalent metal cation 206 may be nickel ($Ni^{2+}$), cobalt ($Co^{2+}$), copper ($Cu^{2+}$), or zinc ($Zn^{2+}$). In one implementation, the divalent metal cation 206 is $Cu^{2+}$. The divalent metal cation 206 may be provided in solution as a salt. For example, $Cu^{2+}$ may be provided by any water-soluble copper (II) salt such as cupric chloride, cupric acetate, or cupric sulfate.

The polymerase that includes a His-tag sequence 204 may be initially complexed with a blocking group 200 through the His-tag sequence 204. The blocking group 200 may be an inactive protein or other polymer of sufficient size to prevent, or greatly reduce, the activity of the polymerase. In an implementation, the blocking group 200 has a molecular weight that is between about 0.5-10× the molecular weight of the polymerase. In an implementation, the blocking group 200 has a weight that is about the same as the polymerase. The template-independent polymerase TdT weighs about 58 kD and includes about 500 amino acids. Thus, in some implementations the blocking group 200 may have a molecular weight of about 50-600 kD. If the blocking group 200 is a protein, its length may be about 50-600 amino acids. In an implementation the molecular weight of the blocking group may be about 58 kD. In an implementation, if the blocking group 200 is a protein its length may be about 500 amino acids.

The blocking group 200 may be covalently modified with a ligand 202 that complexes with the divalent metal cation 206 and the His-tag sequence 204. The ligand 202 may be, for example, a poly(nitrilotriacetic acid) tag (NTA) or an iminodiacetic acid tag (IDA). Techniques for attaching an NTA tag or an IDA tag to a protein or polymer are known to those of skill in the art. Illustrative techniques for attaching NTA tags to other molecules are described in Russell P. Goodman et al., *A Facile Method for Reversibly Linking a Recombinant Protein to DNA,* 10(9) ChemBioChem 1551 (2009).

The complex between the His-tag sequence 204 and the ligand 202 is broken if the divalent metal cation 206 is changed to a different oxidation state. For example, the divalent metal cation 206 may be changed to a monovalent metal cation 208. As a further example, $Cu^{2+}$ may be reduced to $Cu^{+}$. The blocking group 200 will then disassociate from the polymerase leaving active polymerase 108. The process is reversible. If a suitable divalent metal cation 206 becomes available, the blocking group 200 will reattach via the His-tag sequence 204—ligand 202 complex and make the polymerase inactive.

Reduction or oxidation of the divalent metal cation 206 may be achieved by any number of mechanisms. Activation of an electrode such as in a microelectrode array can create a localized change in redox conditions causing the reduction or oxidation of a divalent metal cation 206. For example, a potential of about +0.16 V vs. standard hydrogen electrode (SHE) in an aqueous solution can reduce $Cu^{2+}$ to $Cu^{+}$. A potential of about −0.25 V vs. SHE in an aqueous solution can reduce $Ni^{2+}$ to $Ni^{0}$.

The redox reaction may be initiated directly or indirectly at an electrode surface. At the electrode surface, reduction or oxidation will take place using electron transfer directly at the electrode or mediated by the redox of a mediator. Redox mediators are chemicals with electrochemical activity. In a bioelectrocatalysis process, mediators may exchange electrons with fuels or oxidants at the reaction sites of the biocatalysts, and then diffuse to the surface of electrode and exchange electrons there. Use of mediators may also reduce the required electrode potential which in turn reduces the energy needed to change the divalent metal cation 206 into a monovalent metal cation 208 or other oxidation state.

Additionally, application of a redox reagent by a fluid deposition instrument such as a chemical inkjet printer may be used to reduce or oxidize the divalent metal cation 206 at selected locations on the surface of an array. The redox reagent contributes or receives electrons from the divalent metal cation 206 changing it to a different oxidation state. For example, the reducing agent such as ascorbic acid (e.g., provided as a salt such as sodium ascorbate), citric acid, sodium hypophosphate, hydrazine, including their salts, or similar may be added to reduce $Cu^{2+}$ to $Cu^{+}$. The oxygen may be present as dissolved atmospheric oxygen in the reaction reagent solution or may be provided such as the addition of hydrogen peroxide. The volume of redox agent added is determined by the capabilities of the fluid deposition instrument and the size of area over which the polymerase is to be activated. The concentration of the redox reagent is determined in part by the volume used and the concentration of divalent metal cations 206 in solution. For example, the redox reagent may be added such that the at the selected location there is about 0.1-10 mole equivalents to the divalent metal cations 206. In an implementation, the redox reagent and the divalent metal cations 206 are present in about equimolar amounts at the selected location.

A reduction or oxidation of the divalent metal cation 206 may also be induced by exciting a light-activated photoredox catalyst. The photoredox catalyst may be, for example, a metal polypyridyl complex such as an iridium polypyridyl complex. Any other type of suitable photoredox catalyst may also be used such as, for example, organic photoredox catalysts some of which are described in Nathan A. Romero and David A. Nicewicz, *Organic Photoredox Catalysis,* 116(17) Chem. Rev. 10075 (2016). Light that excites the photoredox catalyst may be directed onto selected locations on an array to provide spatially addressable activation of the polymerase. The photoredox catalysts may be included in the reaction reagent solution. The photoredox catalyst may be added such that the at the selected location there is about 0.1-1 mole equivalents to the divalent metal cations 206.

The change from inactive polymerase 106 to active polymerase 108 is confined to a selected location on the surface of the array by an excess of divalent metal cations 206 and optionally also an excess of blocking groups 200 in the reaction reagent solution. As active polymerase 108 diffuses away from the selected location, the excess divalent metal cations 206 and blocking groups 200 will cause a blocking group 200 to reattach changing the active polymerase 108 back into inactive polymerase 106. This provides spatial control of polymerase activity. For example, using this technique active polymerase 108 may be confined to one or more of the spots 102 shown in FIG. 1.

Additionally, if an electrode is used to change the oxidation state of the divalent metal cation 206, the excess of divalent metal cations 206 will cause the blocking groups 200 to reattach once the current is turned off thereby stopping polynucleotide extension at the selected location. The duration of electrode activation may be used to limit the time that active polymerase 108 is available and thus regulate the extension length.

The divalent metal cations 206 that complex with the His-tag sequence 204 are not the only divalent metal cations in the reaction reagent solution. The polymerase complexes with a cofactor that is also a divalent metal cation. A template-independent polymerase such as TdT is able to use a variety of divalent metal cations such as $Co^{2+}$, $Mn^{2+}$, $Zn^{2+}$ and $Mg^{2+}$. However, due to the difference in chelating groups and steric environments, a redox potential sufficient to reduce (or oxidize) the divalent metal cation 206 chelated to a His-tag sequence 204 is lower than the redox potential needed to change the oxidation state of a metal cofactor complexed with an enzyme. See Scott E. Waters et al., *Effect of Chelation on Iron-Chromium Redox Flow Batteries,* 5 ACS Energy Lett. 1758 (2020) and Yasukazu Yoshida et al., *Effects of metal chelating agents on the oxidation of lipids induced by copper and iron,* 1210 Biochimica et Biophysica Acta 81 (1993). Thus, the same metal ion may be in the His-tag linkage and as an enzyme cofactor by selecting a redox potential sufficient to cause disassociation of the His-tag linkage without changing the oxidation state of the metal cofactor.

In an implementation, the metal cofactor and the divalent metal cation 206 may be selected so that they are different metals. For example, if a cobalt ($Co^{2+}$) metal cofactor is provided for the polymerase, then the divalent metal cation 206 complexed with the His-tag sequence 204 is a different metal cation such as copper ($Cu^{2+}$). The reduction potential of $Co^{2+}$ to Co is −0.28 V vs. SHE as compared to +0.16 V vs. SHE for $Cu^{2+}$ to $Cu^{+}$. Thus, even if both metal ions were in the same environment, the voltage applied by an electrode or the amount and strength of redox reagent or photoredox catalyst that reduce $Cu^{2+}$ will not change the oxidation state of $Co^{2+}$.

Figure 3:
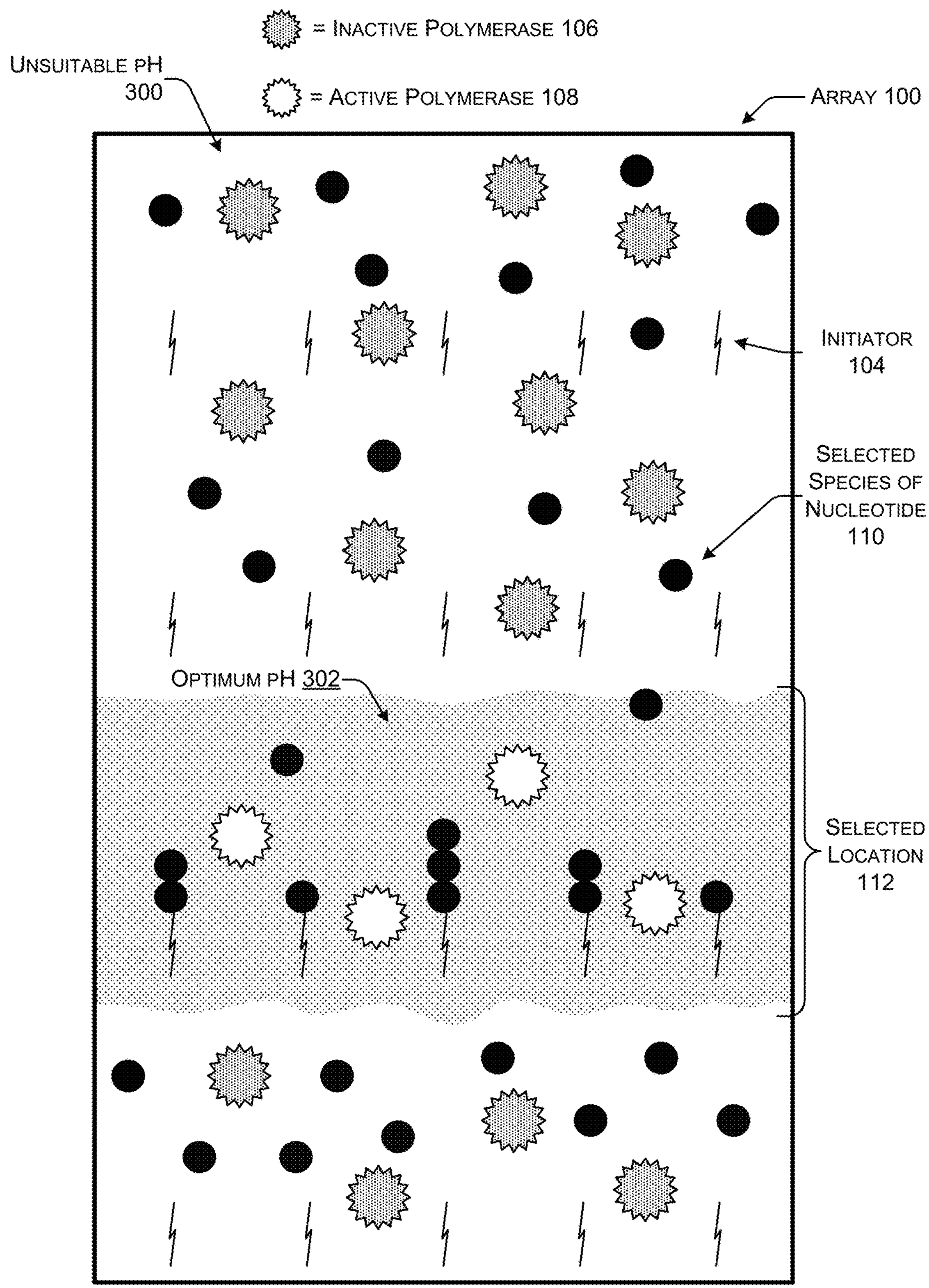
FIG. 3 shows an array for solid-phase polynucleotide synthesis on which spatial control of polymerase activity is regulated by pH.

FIG. 3 shows an array 100 for solid-phase polynucleotide synthesis on which spatial control of polymerase activity is regulated by pH. The array 100 is coated with a plurality of initiators 104. The array 100 may initially be contacted with a reaction reagent solution buffered to an unsuitable pH 300 and inactive polymerase 106. The unsuitable pH is sufficiently acidic or basic to change the conformation of the polymerase in a way that decreases or eliminates enzyme activity. For example, an unsuitable pH for TdT may be below about 4 or above about 10. A selected species of nucleotide 110 is added either together with the reaction reagent solution or separately. Due to the inactivating effects of the unsuitable pH 300, polymerization does not occur or is very slow. Thus, inactive polymerase 106 is present where the pH is an unsuitable pH 300.

The pH of solution contacting the array 100 is changed to an optimum pH 302 for the polymerase at the selected location 112. The selected location 112 may be any shape and may cover any portion of the array 100. In an implementation, the selected location 112 may be one or more spots 102 as illustrated in FIG. 1. Optimum ranges of pH for enzyme activity are known to those of ordinary skill in the art and may be found in F. J. Bollum, In: The Enzymes, Boyer, P.D., ed, Academic Press, New York, 145 (1974). The optimum pH 302 for TdT is about 6-8 pH.

In one implementation, the initial pH of the reaction reagent solution is an unsuitable pH 300 that is higher than the optimum pH 302. The pH is then reduced at the selected location 112 by addition of acid with a targeted deposition instrument. Alternatively, light may be used to activate photoacid generators at the selected location 112 to reduce the pH to the optimum pH 302 for the polymerase. As used herein, photoacid generators include both photoacid generators (irreversible proton photon dissociation) and photoacids (reversibly recombine when exposure to the light source ceases). Many suitable photoacid generators are known including phenols, napthols, and pyrenes (see Heike Kagel et al., *Photoacids in biochemical applications,* 4 J. Cell. Biotech. 23 (2018)). Suitable photoacid generators include photosensitive-2-nitrobenzyl esters (see Pawel J. Serafinowski and Peter B. Garland, *Novel Photoacid Generators for Photodirected Oligonucleotide Synthesis,* 125(4) J. Am. Chem. Soc. 962 (2003)). Suitable water-soluble photoacid generators are also known (see Zheng Shi et al., *Long-Lived Photoacid Based upon a Photochromic Reaction,* 133(37) J. Am. Chem. Soc. 14699 (2011)).

In one implementation, the initial pH of the reaction reagent solution is an unsuitable pH 300 that is lower than the optimum pH 302. The pH is then increased at the selected location 112 by addition of base with a targeted deposition instrument. Alternatively, light may be used to activate photobase generators at the selected location 112 to increase the pH to the optimum pH 302 for the polymerase. Examples of suitable photobase generators tetraphenylborate salt of bicyclic guanidine base, 1,5,7-triaza-bicyclo [4.4.0]dec-5-ene (TBD) (Cheng B. Cao, et al., *Photo-induced crosslinking of water-soluble polymers with a new photobase generator,* 51(18) Polymer, 4058 (2010) and WPBG-266 which is water-soluble and available from Fuji-Film Wako Pure Chemical Corporation.

Electrodes, such as a microelectrode array, may also be used to change the pH of an aqueous solution. The pH of water can be modified electrochemically over a wide range. The maximum concentration limits of base and acid that can be produced in a given water sample limit the range of pH changes. These limits are determined by the kinds and concentrations of all elements dissolved in the water. It is possible, using electricity, to produce water with any content of base or acid within these limits. Electrochemical pH control is based on electrical decomposition of water in an electrolytic cell divided by an ion-exchange membrane or diaphragm into anode and cathode compartments. The minimum (theoretical) voltage necessary to decompose water is 1.23 V at 25° C. Actual decomposition voltage is higher because of the irreversible nature of electrodes. A visible evolution of gases ($O_2$ and $H_2$) commences at 1.7 V. See Albert Regner, *Electrochemical processes in chemical industries*. Artia, Prague: 198-212 (1957). Usually either the anodic or the cathodic reaction is used for pH control, while the complementary reaction may be undesired in some practical applications. An appropriate voltage is applied to a subset of electrodes at the selected location 112 so as to generate an optimum pH 302 in local environment immediately around the electrodes.

The pH change is confined to the selected location 112 by buffer in the solution (e.g., reaction reagent solution) in contact with the array 100. The strength of the buffer affects the degree of confinement. Active polymerase 108 incorporates the selected species of nucleotide 110 on to the ends of the initiators 104 at the selected location 112. If the selected species of nucleotide 110 is an unmodified nucleotide, due to its ability to perform unregulated addition the polymerase may add multiple nucleotides to the ends of the initiators 104.

Figure 4:
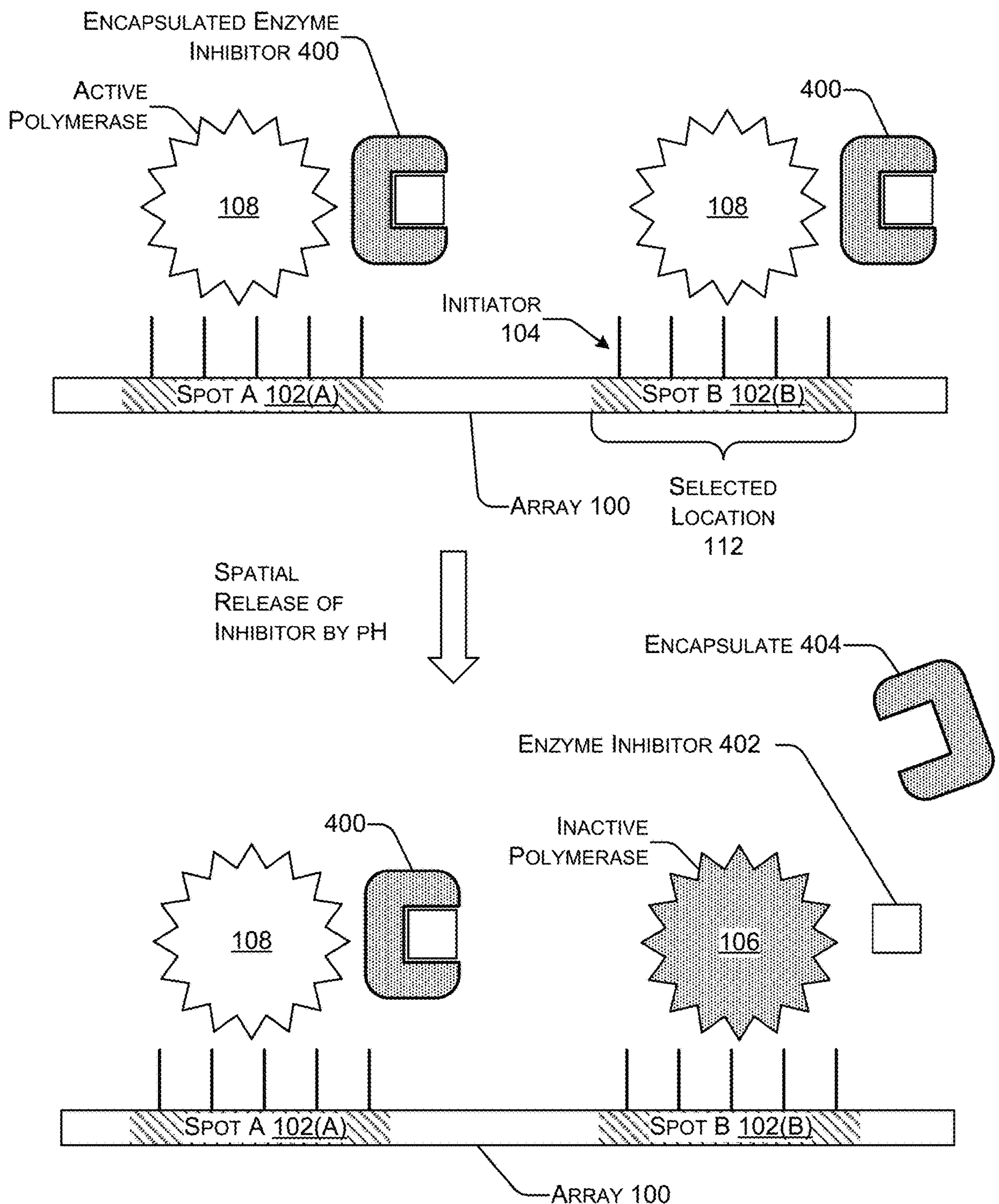
FIG. 4 shows an array for solid-phase polynucleotide synthesis on which spatial control of polymerase activity is regulated by release of encapsulated enzyme inhibitors.

FIG. 4 shows an array 100 for solid-phase polynucleotide synthesis on which spatial control of polymerase activity is regulated by release of encapsulated enzyme inhibitors 400. Initiators 104 are attached to the surface of the array 100 as in the other implementations. A solution contacting the array, e.g., the reaction reagent solution, contains encapsulated enzyme inhibitors 400. The enzyme inhibitor 402 may be any type of inhibitor that, for a particular polymerase, changes it from an active polymerase 108 to an inactive polymerase 106. Numerous enzymatic inhibitors 402 are known to those of ordinary skill in the art. Enzymatic inhibitors 402 that are known to inhibit TdT include ATP and its dinucleotide analogs. See Pandey, V. N., Amrute, S. B., Satav, J. G. and Modak, M. J., *Inhibition of terminal deoxynucleotidyl transferase by adenine dinucleotides*, FEBS Letters, 213 (1987).

The encapsulate 404 cages the enzyme inhibitor 402 and prevents its inhibitory action. Many different techniques are known to those of ordinary skill in the art for pH-dependent encapsulation of a drug or other compound. There are many established systems for encapsulating drugs including hydrogels, nanoparticles, microspheres, acid-cleavable micelles, and amphiphilic assemblies. Some examples are described in Lin Liu et al., pH-Responsive carriers for oral drug delivery: challenges and opportunities of current platforms, 24:1 Drug Delivery, 569 (2017). Any of these techniques, or others, may be adapted to encapsulate an enzyme inhibitor such as ATP. For example, ATP has been encapsulated in liposomes as described in W. Liang, et al., Encapsulation of ATP into liposomes by different methods: optimization of the procedure, 21 (3) J. Microencapsulation 251 (2004).

The pH at a selected location 112 on the array 100, for example spot B 102(B), is changed thereby causing the encapsulate 404 to relate the enzyme inhibitor 402 and create inactive polymerase 106. The pH at the selected location 112 may be changed by any of the techniques mentioned previously. The specific pH change required depends on the encapsulate 404 and can be readily identified by one of ordinary skill in the art. The pH changes to trigger opening of encapsulates 404 may occur at any pH even an unsuitable pH for the polymerase because the unsuitable pH would have synergistic effect with the enzyme inhibitor 402.

With the use of encapsulated enzyme inhibitors 400, polymerase activity is inhibited or stopped at the selected location 112. Thus, prior to release of the enzyme inhibitors 402, active polymerase 108 may be present across the entire surface of the array 100. To prevent undifferentiated incorporation of nucleotides, polymerase activity may be suppressed across the entire array 100 prior to release of the enzyme inhibitors 402. One technique for reducing polymerase active is cooling to a temperature that prevents or greatly slows activity of the polymerase.

The temperature of the aqueous solution contacting the array 100 may be cooled to a temperature a few degrees above freezing. The specific freezing temperature will depend on the concentration and type of salts and buffers in solution. For example, a reaction reagent solution containing the polymerase may be cooled to about 1, 2, 3, 4, 5, 6, 7, 8, 9, or 10° C. prior to mixing with the selected species of nucleotide. Then, after a change in pH has released the enzyme inhibitors 402 at the selected location 112, the temperature is increased to a temperature at which the polymerase is active.

The temperature of all the solution in contact with the array 100 may be increased by use of a heater such as a resistor. If electrodes are used to change the pH and release the enzyme inhibitors 402, the current passing through the reaction reagent solution alone may be sufficient to increase the temperature at the selected location 112.

Even when heated, the polymerase remains inactive polymerase 106 at the locations where the enzyme inhibitor 402 is released. Thus, in this implementation, polynucleotide extension is inhibited at the selected location 112 and the initiators 104 are extended at locations other than the selected location 112. Inhibition may not be complete. There may be some polymerization at the selected location 112. For example, active polymerase 108 may be in contact with the entire array 100 for a brief period of time during each synthesis cycle. The enzyme inhibitors 402 may also diffuse away from the selected location 112 and reduce polymerization at off target areas. However, differences in the amount of polymerization, such as the length of extension regions 114, will be detectably different at the selected location 112 and other areas of the array 100.

Polynucleotides that have the same sequence of nucleotide blocks but differ in the length of the blocks are useful for applications such as encoding information for digital data storage.

Illustrative Process

Figure 5:
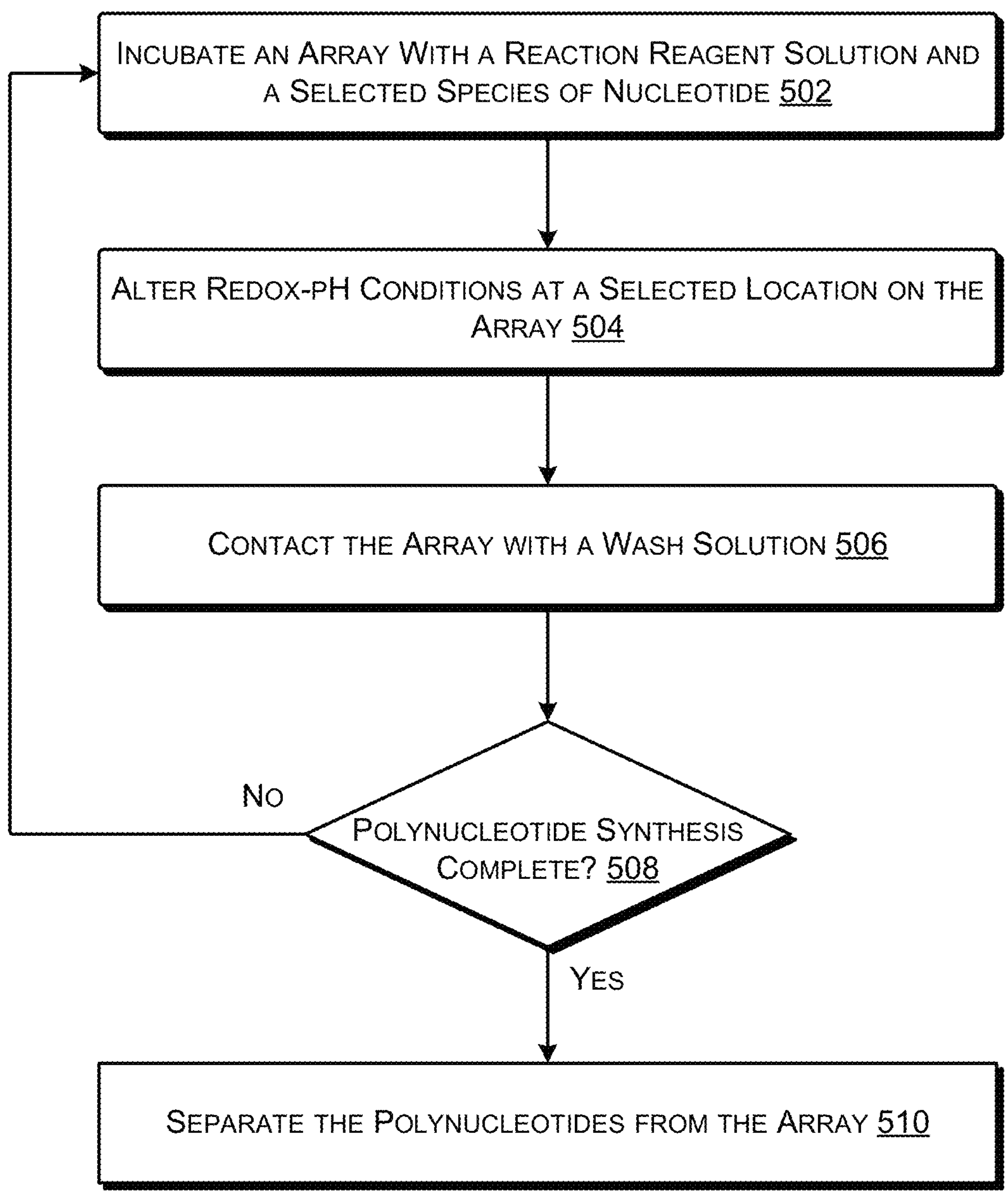
FIG. 5 is a flow diagram showing an illustrative process for solid-phase polynucleotide synthesis using redox-pH conditions to provide spatial control of polymerase activity.

FIG. 5 shows process 500 for de novo synthesis of polynucleotides by spatial control of polymerase activity. This process 500 may be implemented, for example, using any of the processes, techniques, or reactions, shown in FIGS. 1-4 or the device shown in FIG. 6.

At operation 502, an array is incubated with a reaction reagent solution that includes template-independent polymerase and a selected species of nucleotide. The array may be made out of silicon dioxide, glass, an insoluble polymer, or other material. In an implementation, the array is a microelectrode array. In some implementations, the template-independent polymerase is TdT.

A plurality of initiators are attached to the surface of the array. The array may be covered with many thousands or millions of separate initiators. The initiators are single-stranded nucleotides with a length of between about 3-30 bases. Each of the initiators may be identical having the same length and nucleotide sequence. However, there may also be variation among the initiators in terms of length as well as sequence. In some implementations, the sequences of the initiators may include a cut site for restriction enzymes or other nucleases to cleave the polynucleotides from the surface of the array. In some implementation, the initiators may serve as primer binding sites for subsequent amplification of the polynucleotides synthesized on the array.

The template-independent polymerase uses the initiators as a starting point for addition of additional nucleotides to the 3' terminal nucleotide at the end of each initiator. The initiators may be attached to the array by any known or later developed technique for anchoring single-stranded DNA or RNA to a solid support. Example techniques include those used in conventional solid-phase synthesis of DNA and used for creation of DNA microarrays.

The reaction reagent solution may be delivered to a reaction chamber that contains the array. The reaction reagent solution may be added to the reaction chamber by a manual technique such as pipetting. The reaction reagent solution may be added to the reaction chamber by an automated or mechanized system such as via a fluid delivery pathway. The reaction reagent solution includes a substrate-independent polymerase in an appropriate buffer or salt solution.

In one implementation, only unmodified nucleotides are incubated with the reaction reagent solution. For example, the selected species nucleotide may be one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP).

Incubation continues for a length of time referred to as a reaction time. The reaction time may be any length of time sufficient for polymerization to occur. Until activity of the template-independent polymerase is stopped, increased reaction time increases the extension length. For example, the reaction time may be about 10, 20, 30, 40, 50 seconds, 1 minute, or 2 minutes.

Activity of the template-independent polymerase is stopped at the end of the reaction time. The length of time until activity of the template-independent polymerase is stopped may define the reaction time. In an implementation, activity of the template-independent polymerase is stopped by a wash step that removes the template-independent polymerase and the free nucleotides from the surface of the array.

At operation 504, the redox-pH condition is altered at a selected location on the array. A change in redox-pH conditions includes a change in redox conditions or a change in pH conditions. Altering the redox-pH condition affects the activity of the polymerase. The polymerase may be changed from an inactive polymerase that does not perform appreciable nucleotide polymerization to an active polymerase that adds nucleotides to the end of a growing polynucleotide strand. An inactive polymerase may have a rate of polymerization that is decreased to zero or to a level that is statistically distinguishable from active polymerase. The rate of polymerization may be effectively zero if the rate is sufficiently slow such that the polymerase does not incorporate nucleotides during the time when the array is in contact with the reaction reagent solution (e.g., one minute or less). In an implementation, changing the activity of the template-independent polymerase means increasing or decreasing the rate of polymerization activity by at least one order of magnitude.

The selected location may be any one or more locations that are contiguous or separate on the surface of the array. The selected location on the array may be one or more spots that each contain multiple individual initiators such as the spots 102 illustrated in FIG. 1. The selected location may be a single spot, a group of spots located adjacent to each other, or multiple disparate spots spread across the surface of the array in any pattern. The selected location may be changed one or more times during the synthesis of polynucleotides on the array.

Any one of multiple different techniques may be selected to alter the redox-pH conditions on the array. The redox-pH conditions may be altered in a spatially addressable way by activating electrodes on a microelectrode array; adding a redox reagent, acid, or base with a targeted fluid deposition instrument; or exposing a photoredox catalyst, a photoacid, or a photobase in solution to a light source. The light source may be directed onto the array in a site-specific manner by a photomask, digital micromirror device (DMD), or other type of optoelectronics. The photoredox catalyst, photoacid, or photobase may be included in the reaction reagent solution.

In one implementation, a change in redox conditions is used to activate the polymerase at the selected location by causing the release of a blocking group that prevents polymerase activity. Activating the polymerase results in an increase in the rate of polymerization activity. A blocking group may be attached to the polymerase by a His-tag complexed with divalent metal cations. A change in redox conditions at the selected location may cause a localized change in the oxidation state of the metal cations leading to release of the blocking group. The change in redox conditions may be induced by one or more electrodes of a microelectrode array applying a potential of about +0.2, +0.3, or +0.4 V vs SHE. The change in redox conditions may be induced by a redox reagent applied to the surface of the array by a targeted fluid deposition instrument. The redox reagent may be, for example, ascorbic acid, citric acid, sodium hypophosphate, hydrazine, or similar. The change redox conditions may be induced by photo activation of a photoredox catalyst. The photoredox catalyst may be, for example, a metal polypyridyl complex.

In one implementation, a change in pH conditions is used to activate the polymerase at the selected location by changing the pH to an optimum pH for the enzyme. The pH may be maintained across substantially the entire surface of the array at an unsuitable pH to prevent enzyme activity. The pH is then raised or lowered at the selected location into the range of optimum pH for the polymerase. The pH may be changed by activation of electrodes in a microelectrode array, by addition of an acid or base from a targeted fluid deposition instrument, or by activation of a photoacid or photobase upon exposure to a light source.

In one implementation, the change in pH conditions is used to inactivate the polymerase at the selected location by releasing enzyme inhibitors from encapsulation that inhibits activity of the polymerase. Inactivating the polymerase results in a decrease in the rate of polymerization activity. Encapsulates that prevent enzyme inhibitors from interacting with the polymerase may respond to changes in pH. A sufficient change in the pH for the specific type of encapsulate will cause it to release enzyme inhibitors. The localized pH at a selected location may be changed by any of the techniques described above. Thus, there will be inactive polymerase at the selected location and there will be active polymerase at other locations on the array. The encapsulated enzyme inhibitors may be provided in the reaction reagent solution.

Regulation of enzyme activity by encapsulated enzyme inhibitors may be combined with regulation through control of temperature. Temperature may be used to prevent or slow polymerase activity until the enzyme inhibitors are released from encapsulation. For example, the temperature of the reaction reagent solution may be maintained at a low temperature that decreases polymerase activity until the enzyme inhibitors are released and then increased to a suitable temperature for the polymerase. This can prevent nucleotide addition from occurring over the whole array prior to release of the enzyme inhibitors.

At operation 506, the array is contacted with a wash solution. The wash solution may be flowed across the entire array displacing the polymerase and any free nucleotides thereby stopping further extension of the growing polynucleotide strands. Washing between separate cycles of synthesis also prevents contamination of free nucleotides from a previous cycle. The wash solution may be water such as DI (deionized) water. The wash solution may be an aqueous solution that contains at least one of a salt or a buffer. The buffer may be any one of a number of aqueous buffers known to those of ordinary skill in the art that are compatible with polymerases and single-stranded nucleotides such as phosphate-buffered saline (PBS) or tris-buffered saline (TBS). The wash solution may also include a denaturing agent such as a surfactant (e.g., 1% sodium dodecyl sulfate) or a protease (e.g., Proteinase K) to inactivate enzymes on the array.

At operation 508, it is determined if polynucleotide synthesis is complete. If all nucleotides needed to create the specified sequences of the polynucleotides being synthesized on the array have been added, then polynucleotides synthesis is complete. If complete, process 500 proceeds along the "yes" path to operation 510.

If, however, polynucleotide synthesis is not complete, process 500 proceeds along "no" path and returns to 502 where the array is again incubated with a reaction reagent solution and selected species of nucleotide. In a subsequent synthesis cycle the selected location and the species of nucleotide may both be independently changed. Process 500 may be iteratively repeated such that both the selected location and the selected nucleotide are changed at least once between iterations. This allows for the parallel synthesis of multiple polynucleotides each with a different sequence on the surface of a single array.

At operation 510, the polynucleotides are separated from the array. If the polynucleotides are attached to the array by linkers, cleavage of the linkers may release the polynucleotides. The initiators used to start growth of polynucleotides on the array may be cleaved by restriction enzyme digests. Other techniques for separating polynucleotides from a solid substrate following solid-phase synthesis are known to those of ordinary skill in the art. Any suitable technique may be used. The polynucleotides may be collected and stored or processed further such as by amplification with polymerase chain reaction (PCR).

Illustrative System and Device

Figure 6:
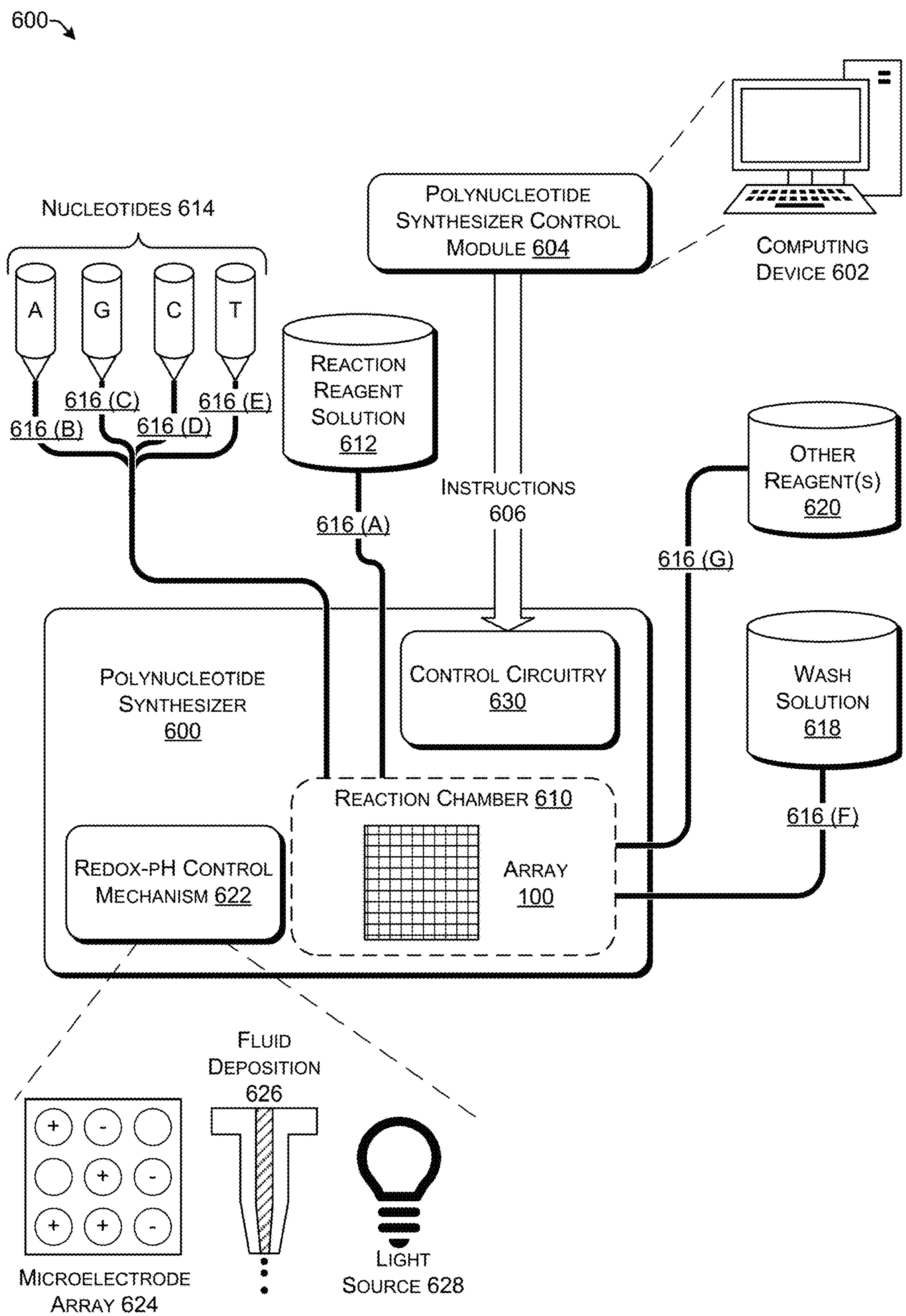
FIG. 6 is an illustrative device for de novo synthesis of polynucleotides.

FIG. 6 is an illustrative system for implementing aspects of this disclosure. The system includes a device for de novo synthesis of polynucleotides that may be referred to as a polynucleotide synthesizer 600. The system may also include a computing device 602. The computing device 602 includes at least one or more processing units and memory such as random-access memory ("RAM") and/or read-only memory ("ROM") communicatively coupled to the processing units. The computing device 602 may also include a mass storage device configured to store files, documents, and data such as, for example, sequence data that is provided to the polynucleotide synthesizer 600 in the form of instructions. The computing device 602 may be implemented as any type of conventional computing device such as a desktop computer, a laptop computer, a server, a hand-held device, or the like. In an implementation, the computing device 602 may be a part of the polynucleotide synthesizer 600 rather than a separate device.

The computing device 602 may include a polynucleotide synthesizer control module 604. The polynucleotide synthesizer control module 604 provides instructions 606 that can control operation of polynucleotide synthesizer 600. For example, the instructions 606 may communicate to the polynucleotide synthesizer 600 base sequences of polynucleotides for synthesis.

The polynucleotide synthesizer 600 is a device that performs automated solid-phase synthesis of on an array 100. The array 100 may be located within a reaction chamber 610 configured to maintain an aqueous solution such as a reaction reagent solution 612 in contact with the surface of the array 100. The polynucleotide synthesizer 600 may also include a heater to control the temperature of the aqueous solution in the reaction chamber 610. The polynucleotide synthesizer 600 may also include a cooling device such as a fan or thermoelectric cooler (e.g., Peltier device) to lower the temperature of the aqueous solution in the reaction chamber 610. As described above, the temperature may be lowered when introducing polymerase in order to suppress activity until enzyme inhibitors are released.

The array 100 may be formed from one or more of silicon dioxide, glass, an insoluble polymer, a non-reactive metal such as gold, silver, or platinum, or other material. The array 100 may be an electrochemically inert surface or it may include a plurality of spatially addressable microelectrodes. Thus, in an implementation, the array 100 may be a microelectrode array with individually addressable electrodes.

The polynucleotide synthesizer 600 may also include storage tanks, bottles, vials, or other containers or receptacles for storing solutions and reagents used in the synthesis of polynucleotides. One such receptacle may contain the reaction reagent solution 612. The reaction reagent solution 612 is an aqueous solution that contains a template-independent polymerase, metal cofactors for the polymerase, and at least one of a salt or buffer.

The buffer may be any one of a number of known aqueous buffers that are compatible with polymerases such as, for example, PBS. PBS is a water-based salt solution containing disodium hydrogen phosphate, sodium chloride and, in some formulations, may also include one or more of potassium chloride and potassium dihydrogen phosphate. Other examples of aqueous buffers known to those of ordinary skill in the art include HEPES, MOPS, PBST, TAE, TBE, TBST, TE, and TEN. See Vincent S. Stoll & John S. Blanchard, *Buffers: Principles and Practice,* 182 Meth. Enzoml., 24 (1990).

Nucleotides 614 may be stored separately in different receptacles. Each species of nucleotide may be stored in a separate receptacle. If synthesizing DNA, the nucleotides 614 may be dNTPs that include one of the natural bases adenine (A), guanine (G), cytosine (C), or thymine (T). If synthesizing RNA, the nucleotides 614 may be NTPs that include one of the natural bases adenine (A), guanine (G), cytosine (C), or uracil (U). In an implementation the nucleotides are unmodified. In an implementation, the nucleotides are modified to include a blocking group such as a 3'-OH blocking group.

Although four different types of nucleotides 614 are illustrated in FIG. 6, the polynucleotide synthesizer 600 may include fewer types (e.g., omit one of the standard nucleotides) or more types (e.g., include one or more artificial nucleotides). Only one species of nucleotide is provided during each cycle of synthesis to control which nucleotide is next incorporated by the template-independent polymerase into the polynucleotides. However, different ones of the available nucleotides 614 may be introduced during different cycles of synthesis to create a plurality of polynucleotides at different locations each with a different nucleotide sequence.

Both the reaction reagent solution 612 and the nucleotides 614 may be brought into contact with the array 100 by a fluid delivery pathway 616 that has a fluid connection with the reaction chamber 610. A first fluid delivery pathway 616(A) may deliver reaction reagent solution 612 to the reaction chamber 610. A second fluid delivery pathway 616(B) may deliver a selected species of nucleotide 614 to the reaction chamber 610. A third fluid delivery pathway 616(C), fourth fluid delivery pathway 616(D), fifth fluid delivery pathway 616(E) and so on may deliver other species of nucleotides 614 to the reaction chamber 610. The fluid delivery pathways 616 may be implemented by one or more of tubes and pumps, microfluidics, laboratory robotics, manual pipetting, or other techniques that move controlled volumes of fluids from one location to another.

The polynucleotide synthesizer 600 may also include a wash solution 618. The wash solution 618 may be water (e.g., DI (deionized) water) or an aqueous solution that contains at least one of a salt or a buffer. The salt or the buffer may be the same as the salt or buffer used in the reaction reagent solution 612. Alternatively, the salt or the buffer may be a different salt or buffer that is suitable for washing polynucleotides such as PBS or TBS. The wash solution 618 is flowed into the reaction chamber 610 through a fluid delivery pathway 616(F). The wash solution 618 displaces the template-independent polymerase and any free nucleotides 614 in the reaction chamber 610. By removing any free nucleotides 614, the subsequent cycle of polymerization can introduce a different species of nucleotide without contamination from the previous cycle. Multiple cycles of addition of the same nucleotide 614 are possible and may each be followed by a wash step even though the same species of nucleotide is being added.

One or more other reagents 620 may also be included in the polynucleotide synthesizer 600 and brought into contact with the array 100 though a fluid delivery pathway 616(G). The other reagents 620 may include, for example, a deblocking agent to deblock protected nucleotides or a supporting electrolyte.

As discussed above, there are multiple different devices and techniques for controlling polymerase activity on the surface of the array 100 by changing redox-pH conditions. All of these different devices and techniques are referred to collectively as a redox-pH control mechanism 622. Polymerization is promoted at one or more selected locations on the array 100 by increasing the rate of nucleotide polymerization from zero or a negligible level to a level at which the polymerase incorporates free nucleotides onto the end of a growing polynucleotide. This may be thought of as "activating" the polymerase. Polymerization is inhibited at one or more selected locations on the surface of the array 100 by reducing the rate of nucleotide polymerization to zero or a negligible level. This may be thought of as "inactivating" polymerization. The spatial pattern of polymerase activation and inactivation causes location-specific polymerization and enables the creation of polynucleotides with different sequences on the array 100.

The redox-pH control mechanism 622 may be any of a microelectrode array 624, a targeted fluid deposition instrument 626, or a light source 628. The redox-pH control mechanism 622 may be controlled by control circuitry 630. The control circuitry 630 may be implemented as any type of circuitry suitable for controlling hardware devices such as a printed circuit board, microcontroller, a programmable logic controller (PLC), or the like. The control circuitry 630 receives and acts on the instructions 606 provided by the polynucleotide synthesizer control module 604. Thus, the control circuitry 630, through the redox-pH control mechanism 622, can control where nucleotide polymerization occurs on the array 100. The control circuitry 630 may also control the fluid delivery pathways 616. For example, the control circuitry 630 may sequentially open the various fluid delivery pathways 616 according to a preprogrammed sequence received in the instructions 606. Thus, the control circuitry 630 can also control the species of nucleotide 614 that is added during any cycle of synthesis.

If the redox-pH control mechanism 622 is a microelectrode array 624, the control circuitry 630 may be able to set the voltage independently at any (or all) of the electrodes in the microelectrode array 624 in any arbitrary pattern. The microelectrode array 624 may be any of the microelectrode arrays described in this disclosure. In an implementation, the microelectrode array 624 may be used to change the oxidation state of divalent metal cations complexed with His-tags attaching blocking groups to polymerases. For example, changes in electrode potential on the microelectrode array 624 may reduce $Cu^{2+}$ to $Cu^{+}$. This will cause the blocking groups to be released and the polymerase becomes active. In an implementation, the microelectrode array 624 may be used the pH to an optimum pH for the polymerase thereby creating active polymerase. Additionally, a change in pH triggered by activation of the microelectrode array 624 may be used to release enzyme inhibitors from encapsulation.

If the redox-pH control mechanism 622 is a targeted fluid deposition instrument 626, the control circuitry 630 may control the location of a print nozzle and the type of reagent that is dispensed onto the surface of the array 100. Thus, the control circuitry 630 may cause an acid, a base, or a redox reagent, etc. to be dispensed according to any arbitrary pattern across one or more selected locations on the array 100. In this implementation, the array 100 does not need to contain electrodes and may be an electrochemically inert surface.

The targeted fluid deposition instrument 626 may be implemented as any type of equipment or device that can precisely apply small volumes of chemical reagents to specific locations on the surface of the array 100. Examples include a chemical inkjet printing device or precision laboratory robotics. Chemical inkjet printing uses techniques similar to conventional printing to place nanoliter volumes of reagents at specified locations on a two-dimensional surface. Techniques for using inkjet printing to precisely deliver chemical reagents to selected locations on a surface of an array are well-known to those of ordinary skill in the art. See Paul Calvert, *Inkjet Printing for Materials and Devices,* 13(10) Chem. Mater. 3299 (2001).

Any type of chemical inkjet printing may be adapted for use with this disclosure. Inkjet printing can be divided into two categories: (1) drop-on-demand (DoD) or impulse inkjet, where droplets are generated when required; and (2) continuous inkjet, in which droplets are deflected from a continuous stream to a substrate when needed. Inkjet printing can be further subdivided according to the specific means of generating droplets, such as piezoelectric, thermal, and electrostatic. Droplet size involves, typically, volumes ranging from 1.5 pL to 5 nL at a rate of 0-25 kHz for drop-on-demand printers (and up to 1 MHz for continuous printheads).

Electrohydrodynamic jet printing (EHJP) is another printing technology that may be used. EHJP is a high-resolution printing technology where the printed liquid is driven by an electric field. Exposure to an electric field causes mobile ions in a polarizable liquid to accumulate at the liquid surface. Deposited droplets can be as small as 240 nm with spatial accuracy in the hundreds of nm, which is typically an order of magnitude smaller than other inkjet printing technologies. Such small droplet sizes dispense less material with more spatial control, which allows for more selectivity in controlling polymerase activity.

In an implementation, the targeted fluid deposition instrument 626 may deliver a redox agent to the selected location on the array 100. The redox reagent may be a reducing reagent or oxidizing reagent that changes the oxidation state of divalent metal cations complexed to a His-tag sequence. For example, the redox reagent may be a reducing agent such as a salt of ascorbic acid (e.g., sodium ascorbate), a salt of citric acid, a salt of sodium hypophosphate, a salt of hydrazine, or similar. Changing the oxidation state of the divalent metal cations to another oxidation state causes the blocking groups to be released from the His-tag sequence and this activates the polymerase.

The targeted fluid deposition instrument 626 may deliver an acid or a base that changes the pH to an optimum pH for the polymerase thereby creating active polymerase 108 at the selected location. Addition of acid or base by the targeted fluid deposition instrument 626 may be used to create active polymerase 108 by changing the local pH to an optimum pH range for the enzyme. If the reaction reagent solution 612 is buffered to an unsuitable pH for the polymerase the polymerase may be denatured and inactive. Raising or lowering the pH to within the optimum pH range allows the polymerase to return to a native conformation and become active. Nucleotide polymerization is then possible at those locations where the targeted fluid deposition instrument 626 has added the acid or base. The buffering capacity of the reaction reagent solution 612 controls the range over which the added acid or base affects pH. As the buffering capacity increases, the area of effect for added acid or base decreases and spatial control becomes more precise.

In an implementation, the acid or base delivered by the targeted fluid deposition instrument 626 may release an enzyme inhibitor from encapsulation. Encapsulation systems for pH-dependent release of drugs or other small molecules are known to those of ordinary skill in the art and discussed above. Release of the enzyme inhibitor from encapsulation will cause the polymerase at the selected location to become inactive polymerase 106.

If the redox-pH control mechanism 622 is a light source 628, the control circuitry 630 may turn the light source 628 on and off and control where light from the light source 628 contacts the array 100. Light from the light source 628 may be directed or focused on to the surface of the array 100 by optoelectronics such as a photomask or DMD. One example of a DMD that directs light onto an array surface is provided in Howon Lee et al. supra. The light source 628 generates light of a specific wavelength or range of wavelengths. Light from the light source 628 may be used to excite a photosensitive molecule such as a photoredox catalyst, a photoacid, or a photobase. In this implementation, the array 100 does not need to contain electrodes and may be an electrochemically inert surface.

In an implementation, light from the light source 628 is used to change the oxidation state of a divalent metal cation complexed with a His-tag. Light from the light source 628 can excite a photoredox catalyst that performs a photoredox reaction with the metal cation or an intermediary. The light may be of any spectrum that is capable of initiating a photochemical reaction that does not damage the polynucleotides or the template-independent polymerase. In an implementation, the light source 628 generates visible light. One suitable class of photoredox catalyst is the metal polypyridyl complexes of which iridium polypyridyl complexes are one example. These types of photoredox catalysts can perform single electron transfers (SET) as part of a series of reactions that reduce Co(III) to Co(II). See Megan H. Shaw et al., *Photoredox Catalysis in Organic Chemistry,* 81 J. Org. Chem. 5898 (2016). There are also suitable organic photoredox catalysts.

In an implementation, light from the light source 628 activates a photoacid or photobase and changes the pH at the selected location. The change in pH may generate active polymerase 108 by moving the pH at the selected location from an unsuitable pH for the enzyme to an optimum pH. Additionally, if polymerase activity is controlled by encapsulated enzyme inhibitors, the change in pH may be used to trigger location-specific release of the enzyme inhibitors from pH-dependent encapsulation.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used in this document "or" means and/or. For example, "A or B" means A without B, B without A, or A and B. As used herein, "comprising" means including all listed features and potentially including addition of other features that are not listed. "Consisting essentially of" means including the listed features and potentially including additional features that do not materially affect the basic and novel characteristics of the listed features. "Consisting of" means only the listed features to the exclusion of any feature not listed.

Clause 1. A method for enzymatic synthesis of polynucleotides comprising: (a) incubating an array having a plurality of initiators attached thereto with a reaction reagent solution comprising template-independent polymerase and with a selected species of nucleotide; and (b) altering redox-pH conditions at a selected location on the array such that activity of the template-independent polymerase is changed, without changing availability of a metal cofactor complexed with the template-independent polymerase.

Clause 2. The method of clause 1, wherein: the template-independent polymerase includes a His-tag sequence, the reaction reagent solution comprises blocking groups covalently modified with ligands and divalent metal cations that complex with the His-tag sequence and with the ligand, and wherein altering the redox-pH conditions comprises altering redox conditions such that an oxidation state of the divalent metal cation changes thereby releasing the blocking groups from complexes with the template-independent polymerase and increasing activity of the template-independent polymerase at the selected location.

Clause 3. The method of clause 2, wherein the divalent metal cations are selected from the group comprising nickel, cobalt, copper, or zinc.

Clause 4. The method of clause 2, wherein the divalent metal cation comprises $Cu^{2+}$.

Clause 5. The method of any of clauses 2-4, wherein the blocking groups comprise proteins or polymers.

Clause 6. The method of clause 5, wherein the blocking groups have molecular weights that are between about 0.5-10× the molecular weight of the template-independent polymerase.

Clause 7. The method of clause 1, wherein the reaction reagent solution has an unsuitable pH for the template-independent polymerase, and wherein altering the redox-pH conditions comprises altering pH conditions to an optimum pH for the template-independent polymerase thereby increasing activity of the template-independent polymerase at the selected location.

Clause 8. The method of clause 1, wherein the reaction reagent solution comprises encapsulated inhibitors, and wherein altering the redox-pH conditions comprise altering pH conditions such that inhibitors are released from encapsulation at the selected location thereby decreasing activity of the template-independent polymerase at the selected location.

Clause 9. The method of any of clauses 1-8, wherein the array comprises a microelectrode array having a plurality of individually addressable electrodes and altering the redox-pH conditions at the selected location on the array comprises activating at least one of the individually addressable electrodes at the selected location.

Clause 10. The method of any of clauses 1-8, wherein the reaction reagent solution further comprises photoredox catalysts and altering the redox-pH conditions at the selected location on the array comprises exposing the selected location on the array to a wavelength of light that excites the photoredox catalyst.

Clause 11. The method of any of clauses 1-8, wherein altering the redox-pH conditions at the selected location on the array comprises delivering a chemical redox reagent, an acid, or a base, to the selected location with targeted fluid deposition instrument.

Clause 12. The method of any of clauses 1-11, wherein the selected species of nucleotide comprises unmodified nucleotides.

Clause 13. The method of any of clauses 1-12, further comprising: (c) contacting the array with a wash solution that removes the reaction reagent solution.

Clause 14. The method of clause 13, further comprising iteratively repeating steps (a), (b), and (c) such that both the selected location and the selected species of nucleotide change at least once between iterations.

Clause 15. The method of any of clauses 1-14, wherein template-independent polymerase is TdT.

Clause 16. The method of any of clauses 1-15, wherein plurality of initiators comprises initiators having a length of between about 3-30 nucleotides.

Clause 17. The method of any of clauses 1-16, wherein the selected species of nucleotide is one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP).

Clause 18. A method for enzymatic synthesis of a polynucleotide comprising: (a) incubating an array having a plurality of initiators attached thereto with a reaction reagent solution comprising inactive template-independent polymerase comprising a His-tag sequence complexed to a blocking group and with a selected species of nucleotide; and (b) altering redox conditions at a selected location on the array such that an oxidation state of a divalent metal cation complexed with the His-tag sequence changes thereby releasing the blocking group converting the inactive template-independent polymerase into active template-independent polymerase.

Clause 19. The method of clause 18, wherein the divalent metal cation comprises $Cu^{2+}$.

Clause 20. The method of any of clauses 18-19, wherein the array comprises a microelectrode array having a plurality of individually addressable electrodes and altering the redox conditions at the selected location on the array comprises activating at least one of the individually addressable electrodes at the selected location.

Clause 21. The method of any of clauses 18-19, wherein the reaction reagent solution further comprises photoredox catalysts and altering the redox conditions at the selected location on the array comprises exposing the selected location on the array to a wavelength of light that excites the photoredox catalysts.

Clause 22. The method of any of clauses 18-19, wherein altering the redox conditions at the selected location on the array comprises delivering a chemical redox reagent to the selected location with a targeted fluid deposition instrument.

Clause 23. The method of any of clauses 18-22, further comprising: (c) contacting the array with a wash solution that removes the reaction reagent solution; and iteratively repeating steps (a), (b), and (c) such that both the selected location and the selected species of nucleotide change at least once between iterations.

Clause 24. A device for de novo synthesis of polynucleotides, the device comprising: an array having a plurality of initiators attached thereto; a first fluid delivery pathway configured to contact the array with a reaction reagent solution comprising a template-independent polymerase including a His-tag sequence complexed to a blocking group covalently modified with a ligand; a second fluid delivery pathway configured to contact the array with a selected species of nucleotide; and control circuitry configured to alter redox conditions at a selected location on the array changing an oxidation state of divalent metal cations complexed to the His-tag sequence thereby releasing the blocking group from the template-independent polymerase and to selectively open the first fluid delivery pathway and the second fluid delivery pathway.

Clause 25. The device of clause 24, wherein the divalent metal cations comprise $Cu^{2+}$.

Clause 26. The device of any of clauses 24-25, further comprising a reaction chamber configured to maintain the reaction reagent solution in contact with the array.

Clause 27. The device of any of clauses 24-26, further comprising: a third fluid delivery pathway configured to contact the array with a second selected species of nucleotide; and a computing device communicatively coupled to the control circuitry and configured to sequentially activate a redox-pH control mechanism and sequentially open the second fluid delivery pathway and the third fluid delivery pathway according to a preprogrammed sequence.

Clause 28. The device of any of clauses 24-27, wherein the array comprises a microelectrode array having a plurality of individually addressable electrodes and the control circuitry is configured to alter redox conditions by activating at least one of the individually addressable electrodes at the selected location.

Clause 29. The device of any of clauses 24-27, wherein the reaction reagent solution further comprises photoredox catalysts and further comprising a light source configured to direct light to the photoredox catalysts at the selected location on the array.

Clause 30. The device of any of clauses 24-27, further comprising a targeted fluid deposition instrument configured to deliver a redox reagent to the selected location on the array.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents, and/or patent applications throughout this specification. Each of the cited references is individually incorporated herein by reference for its particular cited teachings as well as for all that it discloses.

The invention claimed is:

1. A method for enzymatic synthesis of polynucleotides comprising:

(a) incubating an array having a plurality of initiators attached thereto with a reaction reagent solution comprising template-independent polymerase and with a selected species of nucleotide, wherein the reaction reagent solution has an unsuitable pH for the template-independent polymerase; and (b) altering pH conditions at a selected location on the array such that activity of the template-independent polymerase is changed, without changing availability of a metal cofactor complexed with the template-independent polymerase, wherein altering the pH conditions comprises altering pH conditions to an optimum pH for the template-independent polymerase thereby increasing activity of the template-independent polymerase at the selected location, and wherein altering the pH conditions at the selected location on the array further comprises (i) delivering an acid or a base to the selected location with a targeted fluid deposition instrument, or (ii) exposing a photoacid or photobase in the reaction reagent solution to a light source.

2. The method of claim 1, wherein the selected species of nucleotide comprises unmodified nucleotides.

3. The method of claim 1, further comprising:

(c) contacting the array with a wash solution that removes the reaction reagent solution.

4. The method of claim 3, further comprising iteratively repeating steps (a), (b), and (c) such that both the selected location and the selected species of nucleotide change at least once between iterations.

5. The method of claim 1, wherein the plurality of initiators comprise single-stranded nucleotides with a length of between about 3-30 bases.

6. The method of claim 1, wherein the selected species of nucleotide consists of unmodified nucleotides.

7. The method of claim 1, wherein the light source is directed onto the array by a photomask or digital micromirror device (DMD).

8. A method for enzymatic synthesis of polynucleotides comprising:

(a) incubating an array having a plurality of initiators attached thereto with a reaction reagent solution comprising template-independent polymerase that includes a His-tag sequence and with a selected species of nucleotide, wherein the reaction reagent solution comprises blocking groups covalently modified with ligands and divalent metal cations that complex with the His-tag sequence and with the ligands; and (b) altering redox conditions at a selected location on the array such that activity of the template-independent polymerase is changed, without changing availability of a metal cofactor complexed with the template-independent polymerase, wherein altering the redox conditions comprises altering redox conditions such that an oxidation state of the divalent metal cation changes thereby releasing the blocking groups from complexes with the template-independent polymerase and increasing activity of the template-independent polymerase at the selected location, and wherein (i) the array comprises a microelectrode array having a plurality of individually addressable electrodes and altering the redox conditions at the selected location on the array comprises activating at least one of the individually addressable electrodes at the selected location, (ii) the reaction reagent solution further comprises photoredox catalysts and altering the redox conditions at the selected location on the array comprises exposing the selected location on the array to a wavelength of light that excites the photoredox catalyst, or (iii) altering the redox conditions at the selected location on the array comprises delivering a chemical redox reagent to the selected location with a targeted fluid deposition instrument.

9. The method of claim 8, wherein the plurality of initiators comprises single-stranded nucleotides each with a length of between about 3-30 bases.

10. The method of claim 8, wherein the selected species of nucleotide comprises unmodified nucleotides.

11. The method of claim 8, wherein the selected species of nucleotide consists of unmodified nucleotides.

12. The method of claim 8, further comprising:

(c) contacting the array with a wash solution that removes the reaction reagent solution.

13. The method of claim 12, further comprising iteratively repeating steps (a), (b), and (c) such that both the selected location and the selected species of nucleotide change at least once between iterations.

14. A method for enzymatic synthesis of polynucleotides comprising:

(a) incubating an array having a plurality of initiators attached thereto with a reaction reagent solution comprising template-independent polymerase and with a selected species of nucleotide, wherein the reaction reagent solution comprises encapsulated inhibitors; and (b) altering pH conditions at a selected location on the array such that activity of the template-independent polymerase is changed, without changing availability of a metal cofactor complexed with the template-independent polymerase, wherein altering the pH conditions comprise altering pH conditions such that inhibitors are released from encapsulation at the selected location thereby decreasing activity of the template-independent polymerase at the selected location, and wherein altering the pH conditions at the selected location on the array further comprises (i) delivering an acid or a base to the selected location with a targeted fluid deposition instrument or (ii) exposing a photoacid or photobase in the reaction reagent solution to a light source.

15. The method of claim 14, wherein the plurality of initiators comprises single-stranded nucleotides each with a length of between about 3-30 bases.

16. The method of claim 14, wherein the selected species of nucleotide comprises unmodified nucleotides.

17. The method of claim 14, wherein the selected species of nucleotide consists of unmodified nucleotides.

18. The method of claim 14, wherein the light source is directed onto the array by a photomask or digital micromirror device (DMD).

19. The method of claim 14, further comprising:

(c) contacting the array with a wash solution that removes the reaction reagent solution.

20. The method of claim 19, further comprising iteratively repeating steps (a), (b), and (c) such that both the selected location and the selected species of nucleotide change at least once between iterations.

* * * * *